United States Patent [19]
Vasil et al.

[11] Patent Number: 5,955,330
[45] Date of Patent: Sep. 21, 1999

[54] MEANS FOR ENHANCING GENE EXPRESSION

[75] Inventors: Vimla Vasil; Maureen A. Clancy; Robert J. Ferl; Indra K. Vasil; L. Curtis Hannah, all of Gainesville, Fla.

[73] Assignee: Research Corporation Technologies, Tucson, Ariz.

[21] Appl. No.: 08/483,376

[22] Filed: Jun. 7, 1995

Related U.S. Application Data

[63] Continuation of application No. 08/418,540, Apr. 7, 1995, abandoned, which is a continuation of application No. 08/102,115, Aug. 4, 1993, abandoned, which is a continuation of application No. 07/830,956, Feb. 5, 1992, abandoned, which is a continuation of application No. 07/353,854, May 18, 1989, abandoned.

[51] Int. Cl.$^6$ ............................ C07H 21/04; C12N 15/00
[52] U.S. Cl. .................................. 435/172.3; 435/320.1; 435/419
[58] Field of Search ........................... 435/240.47, 172.1, 435/172.3, 172.2, 320.1; 935/35, 33, 34, 36, 37, 40, 41

[56] References Cited

PUBLICATIONS

Werr, W., W.–B. Frommer, C. Maas and P. Starlinger (1985) "Structure of the sucrose synthase gene on chromosome 9 of Zea mays L.," EMBO J. 4(6):1373–1380.

Sheldon, E., R. Ferl, N. Fedoroff, and L.C. Hannah (1983) "Isolation and Analysis of a Genomic Clone Encoding Sucrose Synthetase in Maize: Evidence for Two Introns in Sh," Mol. Gen. Genet. 190:421–426.

Zack, C.D., R.J. Ferl, L.C. Hannah (1986) "DNA sequence of a shrunken allele of maize: Evidence for visitation by insertional sequences," Maydica XXXI:5–16.

Gilbert, W. (1978) "Why genes in pieces?" Nature 271:501.

Hamer, D.H. and P. Leder (1979) "Splicing and the Formation of Stable RNA," Cell 18:1299–1302.

Gasser, C.S., C.C. Simonsen, J.W. Schilling, and R.T. Schimke (1982) "Expression of abbreviated mouse dihydrofolate reductase genes in cultured hamster cells," Proc. Natl. Acad. Sci. USA 79:6522–6526.

Gruss, P., C.–J. Lau, R. Dhar, and G. Khoury (1979) "Splicing as a requirement for biogenesis of functional 16S mRNA of simian virus 40," Proc. Natl. Acad. Sci. USA 76(9):4317–4321.

Callis, J., M. Fromm, and V. Walbot (1987) "Introns increase gene expression in cultured maize cells," Genes & Development 1:1183–1200.

Silva, E.M., I.J. Mettler, P.S. Dietrich, R.M. Sinibaldi (1988) Genome 30 suppl. 1:72.

Fromm, M., L.P. Taylor, and V. Walbot (1985) "Expression of genes transferred into monocot and dicot plant cells by electroporation," Proc. Natl. Acad. Sci. USA 82:5824–5828.

Hauptmann, R.M., P. Ozias–Akins, V. Vasil, Z. Tabaeizadeh, S.G. Rogers, R.B. Horsch, I.K. Vasil, and R.T. Fraley (1987) "Transient expression of electroporated DNA in monocotyledonous and dicotyledonous species," Plant Cell Reports 6:265–270.

Hauptmann, R.M., M. Ashraf, V. Vasil, L.C. Hannah, I.K. Vasil, and R. Ferl (1988) "Promoter Strength Comparisons of Maize Shrunken 1 and Alcohol Dehydrogenase 1 and 2 Promoters in Mono–and Dicotyledonous Species," Plant Physiol. 88:1063–1066.

Chee, P.P., R.C. Klassy, and J.L. Slighton (1986) "Expression of a bean storage protein 'phaseolin minigene' in foreign plant tissues," Gene 41:47–57.

Weising et al., Ann. Rev. Genetics 22:421–477, 1988.

*Primary Examiner*—Scott W. Houtteman
*Attorney, Agent, or Firm*—Greenlee, Winner and Sullivan, P.C.

[57] ABSTRACT

The present invention provides a novel means for enhancing the expression of genes by the use of the first intron of the Zea mays Sh1 cDNA, functional sequences derived therefrom and/or sequences flanking the first Sh1 intron, placed between the transcription start site and the translation start site of the coding sequence for enhanced expression is sought. The DNA sequences provided herein can be used, for example, to increase protein expression in engineered plant cells or in transgenic plants.

46 Claims, 13 Drawing Sheets

```
              -120        -110        -100        -90         -80         -70
              .           .           .           .           .           .
         GAATTCCCAA  GCTCCGTCAG  CTTGAACGTG  GACCCCTACC  ATCTGCACCA  GCTCGGCACC

-60         -50         -40         -30         -20         -10
              .           .           .           .           .           .
         TCACGCTCGC  AGCGCATGGA  GCCTAGGAGC  AGCTGCCCGT  CTATTTATTG  GTCCCTCTCC 1          10          20          30          40          50
               .           .           .           .           .           .
         CGTCCCAGAG  AAACCCTCCC  TCCCTCCTCC  ATTGGACTGC  TTGCTCCCTG  TTGACCATTG 60          70          80          90         100         110
               .           .           .           .           .           .
         GGGTATGCTT  GCTGCCTTGC  TCTCCTGTTC  ATCTCCGTGC  TAAACCTCTG  TCCTCTGGGT 120         130         140         150         160         170
              .           .           .           .           .           .
         GGGTTTTTGC  TGGGATTTTG  AGCTAATCTG  CTGGTCCCGG  TAGAAAAGAT  CATGTCCCCT 180         190         200         210         220         230
              .           .           .           .           .           .
         GAGCAGCTCA  AGCGCTCGCC  TTAGCCGCGT  CCTTGCCCCC  CGCCATTTTT  GCGGTTTCGG 240         250         260         270         280         290
              .           .           .           .           .           .
         TGTGTTCCCG  TGACTCGCCG  GGTGCGTCAT  CGCCTGAATC  TTGTCTGGGC  TCTGCTGACA 300         310         320         330         340         350
              .           .           .           .           .           .
         TGTTCTTGGC  TAGTTGGGTT  TATAGATTCC  TCTGATCTAA  AACCGTGCCT  GTGCTGCGCA 360         370         380         390         400         410
              .           .           .           .           .           .
         CAGAACTCTC  CCCTGTCCTT  TCCTGGGGTT  TTGGTTACGT  GGTGGTAGTA  AGCTTGGATT 420         430         440         450         460         470
              .           .           .           .           .           .
         TGCACATGGA  TAAAGTTGTT  CTAAGCTCCG  TGGGTTGCTT  GAGATCTTGC  TGTTATTGCG 480         490         500         510         520         530
              .           .           .           .           .           .
         TGCCGTGCTC  ACTTTTTTTG  CAATCCGAGG  AATGAATTTG  TCGTTTACTC  GTTTGGTGG 540         550         560         570         580         590
              .           .           .           .           .           .
         ATTATTAGCG  CGAAAAAAAA  ACTCTTTTTT  TTTTTTGTTC  TTTTACTACG  AAAAGCATCT 600         610         620         630         640         650
              .           .           .           .           .           .
         TCTTGGATTT  TGCTATCTTC  TTTTACTACG  AAAAACTCTT  GAGTCTAGGA  ATTTGAATTT 660         670         680         690         700         710
              .           .           .           .           .           .
         GTGATGTCCA  TTCTTGCAGT  GCGCTGTGCT  TTATTGGGAA  GCCAAATCCT  ATTATTTTCT 720         730         740         750         760         770
              .           .           .           .           .           .
         GCCTCTAGGG  TCTGAATGGA  ATCAGTACTC  TTGAGACAGA  AAATCAATCC  AATCAAGTTG 780         790         800         810         820         830
              .           .           .           .           .           .
         ATTTCTTTCT  TTAAAAATAT  TATCACAGAA  CTAAGTGCTT  GTGCGGAATC  AGTACTGGCT 840         850         860         870         880         890
              .           .           .           .           .           .
         TTTGTTTGGT  GGAGGATCAA  TACTTGCTTT  TGTTTGGGGG  TGGCAACTGT  TTGCTATAA
```

FIG. 1A

```
          900        910        920        930        940        950
           .          .          .          .          .          .
     GATTCCATGT GTTCCTGTTG AGATGAATCA TATATAGTAT AGCTGCATAC TACAAATCTG
          960        970        980        990       1000       1010
           .          .          .          .          .          .
     TTTTTCAAAT TTAGGTTGCT TTGGCATGAT CTATTTTTTT GTCAGACAGA CTTTCTAAGT
         1020       1030       1040       1050       1060       1070
           .          .          .          .          .          .
     GGTAGCTCTT GATTTCTTGT TCTTGTACAA CTGGTGCTGC TGAATCTTGA CCGTATAGCT
         1080       1090       1100       1110       1120       1130
           .          .          .          .          .          .
     CGAATTGCAG TATTCTGAAC CATCGACGCA TGGCTGCCAA GCTGACTCGC CTCCACAGTC
         1140       1150       1160       1170       1180       1190
           .          .          .          .          .          .
     TTCCGGAACG CCTTGGTGCC ACCTTCTCCT CCCATCCCAA TGAACTGATA GCACTCTTTT
         1200       1210       1220       1230       1240       1250
           .          .          .          .          .          .
     CCAGGTGGGC TTACCAAAAT CATATAACTT GCATTTCATT CGGTACTGAA AGTTGTTAAT
         1260       1270       1280       1290       1300       1310
           .          .          .          .          .          .
     TTGTTATTCT CTTCATGCCT GTCTTAATAG CACACCCAGA TGTAAACACG AGATTATGCA
         1320       1330       1340       1350       1360       1370
           .          .          .          .          .          .
     ACTTCTTACT TGGTTTCTTT TGTTGGCACC ATCATGCATG CTAATTGCTA AGGATGTTAC
         1380       1390       1400       1410       1420       1430
           .          .          .          .          .          .
     CTATTCATCC TTGACTCATA TTATCATATG TAATGATTTT ATGATCTCGA GACTATTGAT
         1440       1450       1460       1470       1480       1490
           .          .          .          .          .          .
     TGTGAAGCAT AGTATAGCTG TTCTTCAGTT TTTGTACCCT TTTGTTTTTT TCCTTAAGCT
         1500       1510       1520       1530       1540       1550
           .          .          .          .          .          .
     AGAACTGGTA CAATTTAGTT GATAAGACAG TGTAGTTTGT AGTACGTCAT TTGACAGATT
         1560       1570       1580       1590       1600       1610
           .          .          .          .          .          .
     GTTTGTCTTT AGCTGGTAAA GTGCCATTTA ATATCTGTAT CCTTCAGATC TAATAAAAAG
         1620       1630       1640       1650       1660       1670
           .          .          .          .          .          .
     GATATGAGAT GTCCATCACA AGAGGGGAAA AATTACATGA TCTGAGATGT AACATCCGTT
         1680       1690       1700       1710       1720       1730
           .          .          .          .          .          .
     TTTATTTGTG AAATACCACT TCTACAGGTA TGTTCACCAG GGCAAGGGAA TGCTTCAGCG
         1740       1750       1760       1770       1780       1790
           .          .          .          .          .          .
     CCATCAGCTG CTTGCGGAGT TTGATGCCCT GTTTGATAGT GACAAGGAGA AGTATGCACC
         1800       1810       1820       1830       1840       1850
           .          .          .          .          .          .
     CTTTGAAGAC ATTCTTCGTG CTGCTCAGGT AACACTAGCA CTGCTGAGAT GTCTGCTTGA
         1860       1870       1880       1890       1900       1910
           .          .          .          .          .          .
     GTGCTTGCCA ATTGAAACTA AGGTACTCTT TCTAATTTCC CTTGTCTGCA TATAGGAAGC
```

FIG. 1B

```
      1920       1930       1940       1950       1960       1970
         .          .          .          .          .          .
AATTGTGCTC CCCCCATGGG TTGCACTTGC TATCAGGCCA AGGCCTGGTG TCTGGGATTA
      1980       1990       2000       2010       2020       2030
         .          .          .          .          .          .
CATTCGGGTG AATGTAAGTG AGCTGGCTGT GGAGGAGCTG AGTGTTTCTG AGTACTTGGC
      2040       2050       2060       2070       2080       2090
         .          .          .          .          .          .
ATTCAAGGAA CAGCTGGTGG ATGGACAGTA AGTTCTTTGA TGAATTGATT GTAGTCTTTA
      2100       2110       2120       2130       2140       2150
         .          .          .          .          .          .
GCTATGTCTA TATTCTAGTT ATACTAATTC GAGTCCTTTT TTACCAGATC CAACAGCAAC
      2160       2170       2180       2190       2200       2210
         .          .          .          .          .          .
TTTGTGCTTG AGCTTGATTT TGAGCCCTTC AATGCCTCCT TTCCTCGTCC TTCCATGTCG
      2220       2230       2240       2250       2260       2270
         .          .          .          .          .          .
AAGTCCATCG GAAATGGAGT GCAATTCCTT AACCGACACC TGTCGTCCAA GTTGTTCCAG
      2280       2290       2300       2310       2320       2330
         .          .          .          .          .          .
GACAAGGAGA GTTTGTACCC CTTGCTGAAC TTCCTCAAGG CTCATAACTA CAAGGGCACG
      2340       2350       2360       2370       2380       2390
         .          .          .          .          .          .
GTGAGCTTCC ACAGTCCAGA GTCTTTTAAG CACATGCTTC ACAATGGATG ATGTCAATAT
      2400       2410       2420       2430       2440       2450
         .          .          .          .          .          .
TTTCTTACTA TTATCTAGGA ACTTCACATA ACCTGAAATG GATTAATGAT GCCATCTGCA
      2460       2470       2480       2490       2500       2510
         .          .          .          .          .          .
TTATTCTACT GCTGTTTCGT ACAGACGATG ATGTTGAATG ACAGAATCCA AAGCCTTCGT
      2520       2530       2540       2550       2560       2570
         .          .          .          .          .          .
GGTCTCCAAT CATCCCTGAG AAAGGCAAAG GAGTATCTAC TGAGTGTTCC TCAAGACACT
      2580       2590       2600       2610       2620       2630
         .          .          .          .          .          .
CCCTACTCGG AGTTCAACCA TAGGTGAATG CTCAATAAAA CGTTCTGTAC TTGCTATGGA
      2640       2650       2660       2670       2680       2690
         .          .          .          .          .          .
ACTTTGGTTG AAATATGACA AATGGATTAA CTGCCTATAA TGCCACTATG ATCTGTGTTA
      2700       2710       2720       2730       2740       2750
         .          .          .          .          .          .
GGTTCCAAGA GCTTGGCTTG GAGAAGGGTT GGGGTGACAC TGCGAAGCGT GTACTCGACA
      2760       2770       2780       2790       2800       2810
         .          .          .          .          .          .
CACTCCACTT GCTTCTCGAC CTTCTGGAGG CCCCTGATCC TGCCAACTTG GAGAAGTTCC
      2820       2830       2840       2850       2860       2870
         .          .          .          .          .          .
TTGGAACTAT ACCAATGATG TTCAACGTTG TTATCCTGTC TCCTCATGGC TACTTCGCCC
      2880       2890       2900       2910       2920       2930
         .          .          .          .          .          .
AGTCCAATGT GCTTGGATAC CCTGACACTG GCGGTCAGGT ACAGAAGCTT AGTGATTACT
```

FIG. 1C

```
           2940       2950       2960       2970       2980       2990
             .          .          .          .          .          .
       ATTTCCTTTA GGCTTTGTTT GGGTATAGAG GGATTGAAGT GAATTGAGGT GTATTAAAGA
           3000       3010       3020       3030       3040       3050
             .          .          .          .          .          .
       GGATTGAAAG AAAAATTAGT TTATATTACA CTTCAATACA CCACATACCA CCTCAATCCA
           3060       3070       3080       3090       3100       3110
             .          .          .          .          .          .
       CTCCAATTTG AGATTACCCA AACAAGCCCT TAGCTACTTT CCACTTCCAG GTTTCTCATT
           3120       3130       3140       3150       3160       3170
             .          .          .          .          .          .
       TGCGATCGTT TGCAGGTTGT GTACATTCTG GATCAGGTCC GTGCTTTGGA GAATGAGATG
           3180       3190       3200       3210       3220       3230
             .          .          .          .          .          .
       CTTCTGAGGA TTAAGCAGCA AGGCCTTGAT ATCACTCCGA AGATCCTCAT TGTATGTTTG
           3240       3250       3260       3270       3280       3290
             .          .          .          .          .          .
       AGCCCACGTT TCACCTTCTG AATCCTTTTT TTCACTGTGC CTTGATTTAC TCAGTAAATG
           3300       3310       3320       3330       3340       3350
             .          .          .          .          .          .
       TGCCTACATG ATCTTATTTG TTGCAGGTTA CCAGGCTGTT GCCTGATGCT GCTGGGACTA
           3360       3370       3380       3390       3400       3410
             .          .          .          .          .          .
       CGTGCGGTCA GCGGCTGGAG AAGGTCATTG GTACTGAGCA CACAGACATC ATTCGCGTTC
           3420       3430       3440       3450       3460       3470
             .          .          .          .          .          .
       CCTTCAGAAA TGAGAATGGC ATCCTCCGCA AGTGGATCTC TCGTTTTGAT GTCTGGCCAT
           3480       3490       3500       3510       3520       3530
             .          .          .          .          .          .
       ACCTGGAGAC ATACACTGAG GTATACCGAT TATCTGACTG GATGTCCTAC ACAGCATAGC
           3540       3550       3560       3570       3580       3590
             .          .          .          .          .          .
       ATGTTTGAGT AAATACTGAA GCCATGCATT CTGTGCTGCA GGATGTTTCC AGTGAAATAA
           3600       3610       3620       3630       3640       3650
             .          .          .          .          .          .
       TGAAAGAAAT GCAGGCCAAG CCTGACCTTA TCATTGGCAA CTACAGCGAT GGCAACCTAG
           3660       3670       3680       3690       3700       3710
             .          .          .          .          .          .
       TCGCCACTCT GCTCGCGCAC AAGTTGGGAG TCACTCAGGT CTGTCTGTTT GGTTTTACAT
           3720       3730       3740       3750       3760       3770
             .          .          .          .          .          .
       GAGTATTTGA GTATCTTTAA AATTATTAAG TTATTATTTC AATTGCTTAA TGGTTTTGTA
           3780       3790       3800       3810       3820       3830
             .          .          .          .          .          .
       CATACTTGCA GTGTACCATC GCTCATGCCT TGGAGAAAAC CAAATACCCC AACTCGGACA
           3840       3850       3860       3870       3880       3890
             .          .          .          .          .          .
       TATACTTGGA CAAATTCGAC AGCCAGTACC ACTTCTCTTG CCAGTTCACA GCTGACCTTA
           3900       3910       3920       3930       3940       3950
             .          .          .          .          .          .
       TTGCCATGAA CCACACCGAT TTCATCATCA CCAGCACATT CCAAGAAATC GCGGGAAGGT
```

FIG. 1D

```
                3960       3970       3980       3990       4000       4010
           AGAATTTGTA TATTAGTACG CTGTGCTTTA GTAGTAAATA AAACTAGTAT GTGATGTTTT
                4020       4030       4040       4050       4060       4070
           CTGTGTTGTT TCTGCAGCAA GGACACCGTG GGGCAGTACG AGTCCCACAT CGCGTTCACT
                4080       4090       4100       4110       4120       4130
           CTTCCTGGGC TCTACCGTGT CGTCCATGGC ATCGATGTTT TCGATCCCAA GTTCAACATT
                4140       4150       4160       4170       4180       4190
           GTCTCCCCTG GAGCAGACAT GAGTGTTTAC TACCCGTATA CGGAAACCGA CAAGAGACTC
                4200       4210       4220       4230       4240       4250
           ACTGCCTTCC ATCCTGAAAT CGAGGAGCTC ATCTACAGCG ACGTCGAGAA CTCCGAGCAC
                4260       4270       4280       4290       4300       4310
           AAGTGAGTAT ACTGAAAACT GGTTGCATGT CTTACTGCAG CCAATCAGCT TGTAAATACT
                4320       4330       4340       4350       4360       4370
           CCAACACCCA TCGCATGATC TATCCATCTT TCTATCTGTC ACCTGAGCTG AACACCTGGT
                4380       4390       4400       4410       4420       4430
           GTTTACTTGC ATCCAGGTTC GTGCTGAAGG ACAAGAAGAA GCCGATCATC TTCTCGATGG
                4440       4450       4460       4470       4480       4490
           CGCGTCTCGA CCGCGTGAAG AACATGACAG GCCTGGTCGA GATGTACGGC AAGAACGCGC
                4500       4510       4520       4530       4540       4550
           GCCTGAGGGA GCTGGCGAAC CTCGTGATCG TTGCCGGTGA CCACGGCAAG GAGTCCAAGG
                4560       4570       4580       4590       4600       4610
           ACAGGGAGGA GCAGGCGGAG TTCAAGAAGA TGTACAGCCT CATCGACGAG TACAAGTTGA
                4620       4630       4640       4650       4660       4670
           AGGGCCATAT CCGGTGGATC TCGGCGCAGA TGAACCGCGT CCGCAACGGG GAGCTGTACC
                4680       4690       4700       4710       4720       4730
           GCTACATTTG CGATACGAAG GGCGCATTCG TGCAGGTATA TGCACACACA CACACACACT
                4740       4750       4760       4770       4780       4790
           TGGATCTAAT ATCTAACCTC CCAAGTTCCC ACAACGGTGC AATCTACTTT CAGACAACAA
                4800       4810       4820       4830       4840       4850
           CAGTCACTGA ATCATTTCAT CACTTTGTTT TTTTTTTGTG TGGGTAGCCT GCGTTCTACG
                4860       4870       4880       4890       4900       4910
           AAGCGTTCGG CCTGACTGTG ATCGAGTCCA TGACGTGCGG TCTGCCAACG ATCGCGACCT
                4920       4930       4940       4950       4960       4970
           GCCATGGCGG CCCTGCTGAG ATCATCGTGG ACGGGTATC  TGGCCTGCAC ATTGACCCTT
```

FIG. 1E

```
       4980       4990       5000       5010       5020       5030
ACCACAGCGA CAAGGCCGCG GATATCCTGG TCAACTTCTT TGACAAATGC AAGGCAGATC 5040       5050       5060       5070       5080       5090
CGAGCTACTG GGACAAGATC TCACAGGACG ACCTGCAGAG AATTTATGAG AAGTATGCAT 5100       5110       5120       5130       5140       5150
TTTTTTTCTC TCCTGCCATA CAATGTAAAA TTCTTGTTGA CTGAAGGCGC ATCTGTTTTA 5160       5170       5180       5190       5200       5210
CTCCCACGGA CACTCGGAAA TCTGCCGTAC CCTTCTCTAG TTAGGAGGAG TAGTAAAAAA 5220       5230       5240       5250       5260       5270
ATACTGACAC TACAAGCTTT GGATTGCTCA GGTACACCTG GAAGCTCTAC TCCGAGAGGC 5280       5290       5300       5310       5320       5330
TGATGACCCT GACCGGCGTG TACGGGTTCT GGAAGTACGT GAGCAACCTG GAGAGGCGCG 5340       5350       5360       5370       5380       5390
AGACCCGCCG CTACATCGAG ATGTTCTACG CCCTGAAGTA CCGTAGCCTG GTAAGCCGTT 5400       5410       5420       5430       5440       5450
TGATGCCTGC CTCTGCCTCT GCCTCTGCCT GCTAGAGAGG ATCACGTGCT CGTTCCCATT 5460       5470       5480       5490       5500       5510
CCAGCAGTCT TAAACGAGTG GATGAACTAC TGACGCCTCT CTTTCTGGAA TCCAGGCAAG 5520       5530       5540       5550       5560       5570
CCAGGTTCCG CTGTCCTTCG ATTAGTACGG GGAAAGAAGA AGCCCAGGCC GGAGAACCAT 5580       5590       5600       5610       5620       5630
CGCCTGCATT TCGATCTGTT TCACCGCAAT TCGCATTGTT AGTCGTGTAT TGGAGTTATG 5640       5650       5660       5670       5680       5690
TGTACTTGGT TTCCAAGAAC TTTGGTTCCT TGTTTTTTTT TCTTTCTTGT TTGAGCGTTT 5700       5710       5720       5730       5740       5750
TTGGGCAGCG CTGGCCTGGT TCCTAGTATG GTGGGAATTG GCTGCACCTT TTGCTTCGAA 5760       5770       5780       5790       5800       5810
TAAAAATGCC TGCTCGTTCA CCTGTCTTCC GGAGTGCAAT GGGATGTTCT GACTGATGGC 5820       5830       5840       5850       5860       5870
GATGTTGTGT TCTTCTGTTA ATCGCCTGTT TAACGTGGTA GGCTGATGCT TGTTCTTGTT 5880       5890       5900       5910       5920       5930
GAGAAAGCTT GCTGTGCCAG ACACTGTCTT GAATACAAGT GAAGAAAAAA AAAAGGCATG 5940       5950       5960       5970       5980       5990
CCAAGTAAAG TTGCACAAAA TTTCCAACTG CTCAGTGGAC CACTGGACCA TGTTCTTGGT
```

FIG. 1F

```
         6000       6010       6020       6030       6040       6050
TATAGCAGTT GCAAGGCTTC ACATGGCGTT TGGACAGCAG TCTTGGATTG ATGCATAAAG
         6060       6070       6080       6090       6100       6110
AGGTGGTGGT TAACTGAGGA CGCAAGGCCG TTCCCTCAGA GTCAGTCACA AGGTTGCAGA
         6120       6130       6140       6150       6160       6170
GCTCACGGTT CTCTTCCCTT TCCGCTTCCT GTCACATCGG AATTGTTGTT TACGCCATCA
         6180       6190       6200       6210       6220       6230
GCCCATCACC CACCAAACAC TTAGTTCTAT GTTTCTGTAC TGGATCTTTC AATGCGGAAC
         6240       6250
GCGCTTAGTT CCTTCGTGAC AGTCGA
```

FIG. 1G

```
+1....42 nt....43 nt Polylinker....43 nt....ATG
```

```
     Sma1     Xba1            Acc1  Pst1
GGTACCCGGGGATCCTCTAGAGTCGAGATCCGTCGACCTGCAG
 Kpn1   BamHI                        HincII
```

FIG. 7A

```
CCGACCATTGGGTATTCTGAACCATCGACC    (SEQ ID NO:2)
|  exon 1   |     exon 2      |
```

FIG. 7B

```
GAATCAAGTGCAAAGCTGCGGACGGATC    (SEQ ID NO:3)
|   exon 1   | exon 2 | linker
```

FIG. 7 C

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 6386 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Zea mays
      (B) STRAIN: Black Sweet (ix) FEATURE:
      (A) NAME/KEY: exon
      (B) LOCATION: 131..182

(ix) FEATURE:
    (A) NAME/KEY: exon
    (B) LOCATION: 1211..1324

(ix) FEATURE:
    (A) NAME/KEY: exon
    (B) LOCATION: 1828..1948

(ix) FEATURE:
    (A) NAME/KEY: exon
    (B) LOCATION: 2041..2187

(ix) FEATURE:
    (A) NAME/KEY: exon
    (B) LOCATION: 2269..2460

(ix) FEATURE:
    (A) NAME/KEY: exon
    (B) LOCATION: 2605..2728

(ix) FEATURE:
    (A) NAME/KEY: exon
    (B) LOCATION: 2822..3038

(ix) FEATURE:
    (A) NAME/KEY: exon
    (B) LOCATION: 3256..3351

(ix) FEATURE:
    (A) NAME/KEY: exon
    (B) LOCATION: 3447..3620

(ix) FEATURE:
    (A) NAME/KEY: exon
    (B) LOCATION: 3702..3818

(ix) FEATURE:
    (A) NAME/KEY: exon
    (B) LOCATION: 3912..4078

(ix) FEATURE:
    (A) NAME/KEY: exon
    (B) LOCATION: 4158..4381

(ix) FEATURE:
    (A) NAME/KEY: exon
    (B) LOCATION: 4517..4835

(ix) FEATURE:
    (A) NAME/KEY: exon
    (B) LOCATION: 4768..5212

(ix) FEATURE:
    (A) NAME/KEY: exon
    (B) LOCATION: 5372..5510

(ix) FEATURE:
    (A) NAME/KEY: exon
    (B) LOCATION: 5636..5917

(xi) SEQUENCE DESCRIPTION: SEQ ID NO:1:

```
GAATTCCCAA GCTCCGTCAG CTTGAACGTG GACCCCTACC ATCTGCACCA GCTCGGCACC      60

TCACGCTCGC AGCGCATGGA GCCTAGGAGC AGCTGCCCGT CTATTTATTG GTCCCTCTCC     120

CGTCCCAGAG AAACCCTCCC TCCCTCCTCC ATTGGACTGC TTGCTCCCTG TTGACCATTG     180

GGGTATGCTT GCTGCCTTGC TCTCCTGTTC ATCTCCGTGC TAAACCTCTG TCCTCTGGGT     240

GGGTTTTTGC TGGGATTTTG AGCTAATCTG CTGGTCCCGG TAGAAAAGAT CATGTCCCCT     300

GAGCAGCTCA AGCGCTCGCC TTAGCCGCGT CCTTGCCCCC CGCCATTTTT GCGGTTTCGG     360

TGTGTTCCCG TGACTCGCCG GGTGCGTCAT CGCCTGAATC TTGTCTGGGC TCTGCTGACA     420

TGTTCTTGGC TAGTTGGGTT TATAGATTCC TCTGATCTAA AACCGTGCCT GTGCTGCGCA     480

CAGAACTCTC CCCTGTCCTT TCCTGGGGTT TTGGTTACGT GGTGGTAGTA AGCTTGGATT     540
```

-continued

```
TGCACATGGA TAAAGTTGTT CTAAGCTCCG TGGGTTGCTT GAGATCTTGC TGTTATTGCG    600
TGCCGTGCTC ACTTTTTTTG CAATCCGAGG AATGAATTTG TCGTTTACTC GTTTTGGTGG    660
ATTATTAGCG CGAAAAAAAA ACTCTTTTTT TTTTTTGTTC TTTTACTACG AAAAGCATCT    720
TCTTGGATTT TGCTATCTTC TTTTACTACG AAAAACTCTT GAGTCTAGGA ATTTGAATTT    780
GTGATGTCCA TTCTTGCAGT GCGCTGTGCT TTATTGGGAA GCCAAATCCT ATTATTTTCT    840
GCCTCTAGGG TCTGAATGGA ATCAGTACTC TTGAGACAGA AAATCAATCC AATCAAGTTG    900
ATTTCTTTCT TTAAAAATAT TATCACAGAA CTAAGTGCTT GTGCGGAATC AGTACTGGCT    960
TTTGTTTGGT GGAGGATCAA TACTTGCTTT TGTTTGGGGG TGGCAACTGT TTTGCTATAA   1020
GATTCCATGT GTTCCTGTTG AGATGAATCA TATATAGTAT AGCTGCATAC TACAAATCTG   1080
TTTTTCAAAT TTAGGTTGCT TTGGCATGAT CTATTTTTTT GTCAGACAGA CTTTCTAAGT   1140
GGTAGCTCTT GATTTCTTGT TCTTGTACAA CTGGTGCTGC TGAATCTTGA CCGTATAGCT   1200
CGAATTGCAG TATTCTGAAC CATCGACGCA TGGCTGCCAA GCTGACTCGC CTCCACAGTC   1260
TTCCGGAACG CCTTGGTGCC ACCTTCTCCT CCCATCCCAA TGAACTGATA GCACTCTTTT   1320
CCAGGTGGGC TTACCAAAAT CATATAACTT GCATTTCATT CGGTACTGAA AGTTGTTAAT   1380
TTGTTATTCT CTTCATGCCT GTCTTAATAG CACACCCAGA TGTAAACACG AGATTATGCA   1440
ACTTCTTACT TGGTTTCTTT TGTTGGCACC ATCATGCATG CTAATTGCTA AGGATGTTAC   1500
CTATTCATCC TTGACTCATA TTATCATATG TAATGATTTT ATGATCTCGA GACTATTGAT   1560
TGTGAAGCAT AGTATAGCTG TTCTTCAGTT TTTGTACCCT TTTGTTTTTT TCCTTAAGCT   1620
AGAACTGGTA CAATTTAGTT GATAAGACAG TGTAGTTTGT AGTACGTCAT TTGACAGATT   1680
GTTTGTCTTT AGCTGGTAAA GTGCCATTTA ATATCTGTAT CCTTCAGATC TAATAAAAAG   1740
GATATGAGAT GTCCATCACA AGAGGGGAAA AATTACATGA TCTGAGATGT AACATCCGTT   1800
TTTATTTGTG AAATACCACT TCTACAGGTA TGTTCACCAG GGCAAGGGAA TGCTTCAGCG   1860
CCATCAGCTG CTTGCGGAGT TTGATGCCCT GTTTGATAGT GACAAGGAGA AGTATGCACC   1920
CTTTGAAGAC ATTCTTCGTG CTGCTCAGGT AACACTAGCA CTGCTGAGAT GTCTGCTTGA   1980
GTGCTTGCCA ATTGAAACTA AGGTACTCTT TCTAATTTCC CTTGTCTGCA TATAGGAAGC   2040
AATTGTCTC CCCCCATGGG TTGCACTTGC TATCAGGCCA AGGCCTGGTG TCTGGGATTA    2100
CATTCGGGTG AATGTAAGTG AGCTGGCTGT GGAGGAGCTG AGTGTTTCTG AGTACTTGGC   2160
ATTCAAGGAA CAGCTGGTGG ATGGACAGTA AGTTCTTTGA TGAATTGATT GTAGTCTTTA   2220
GCTATGTCTA TATTCTAGTT ATACTAATTC GAGTCCTTTT TTACCAGATC CAACAGCAAC   2280
TTTGTGCTTG AGCTTGATTT TGAGCCCTTC AATGCCTCCT TTCCTCGTCC TTCCATGTCG   2340
AAGTCCATCG GAAATGGAGT GCAATTCCTT AACCGACACC TGTCGTCCAA GTTGTTCCAG   2400
GACAAGGAGA GTTTGTACCC CTTGCTGAAC TTCCTCAAGG CTCATAACTA CAAGGGCACG   2460
GTGAGCTTCC ACAGTCCAGA GTCTTTTAAG CACATGCTTC ACAATGGATG ATGTCAATAT   2520
TTTCTTACTA TTATCTAGGA ACTTCACATA ACCTGAAATG GATTAATGAT GCCATCTGCA   2580
TTATTCTACT GCTGTTTCGT ACAGACGATG ATGTTGAATG ACAGAATCCA AAGCCTTCGT   2640
GGTCTCCAAT CATCCCTGAG AAAGGCAAAG GAGTATCTAC TGAGTGTTCC TCAAGACACT   2700
CCCTACTCGG AGTTCAACCA TAGGTGAATG CTCAATAAAA CGTTCTGTAC TTGCTATGGA   2760
ACTTGGTTG AAAATATGACA AATGGATTAA CTGCCTATAA TGCCACTATG ATCTGTGTTA    2820
GGTTCCAAGA GCTTGGCTTG GAGAAGGGTT GGGGTGACAC TGCGAAGCGT GTACTCGACA   2880
CACTCCACTT GCTTCTCGAC CTTCTGGAGG CCCCTGATCC TGCCAACTTG GAGAAGTTCC   2940
```

```
TTGGAACTAT ACCAATGATG TTCAACGTTG TTATCCTGTC TCCTCATGGC TACTTCGCCC    3000

AGTCCAATGT GCTTGGATAC CCTGACACTG GCGGTCAGGT ACAGAAGCTT AGTGATTACT    3060

ATTTCCTTTA GGCTTTGTTT GGGTATAGAG GGATTGAAGT GAATTGAGGT GTATTAAAGA    3120

GGATTGAAAG AAAAATTAGT TTATATTACA CTTCAATACA CCACATACCA CCTCAATCCA    3180

CTCCAATTTG AGATTACCCA AACAAGCCCT TAGCTACTTT CCACTTCCAG GTTTCTCATT    3240

TGCGATCGTT TGCAGGTTGT GTACATTCTG GATCAGGTCC GTGCTTTGGA GAATGAGATG    3300

CTTCTGAGGA TTAAGCAGCA AGGCCTTGAT ATCACTCCGA AGATCCTCAT TGTATGTTTG    3360

AGCCCACGTT TCACCTTCTG AATCCTTTTT TTCACTGTGC CTTGATTTAC TCAGTAAATG    3420

TGCCTACATG ATCTTATTTG TTGCAGGTTA CCAGGCTGTT GCCTGATGCT GCTGGGACTA    3480

CGTGCGGTCA GCGGCTGGAG AAGGTCATTG GTACTGAGCA CACAGACATC ATTCGCGTTC    3540

CCTTCAGAAA TGAGAATGGC ATCCTCCGCA AGTGGATCTC TCGTTTTGAT GTCTGGCCAT    3600

ACCTGGAGAC ATACACTGAG GTATACCGAT TATCTGACTG GATGTCCTAC ACAGCATAGC    3660

ATGTTTGAGT AAATACTGAA GCCATGCATT CTGTGCTGCA GGATGTTCC AGTGAAATAA     3720

TGAAAGAAAT GCAGGCCAAG CCTGACCTTA TCATTGGCAA CTACAGCGAT GGCAACCTAG    3780

TCGCCACTCT GCTCGCGCAC AAGTTGGGAG TCACTCAGGT CTGTCTGTTT GGTTTTACAT    3840

GAGTATTTGA GTATCTTTAA AATTATTAAG TTATTATTTC AATTGCTTAA TGGTTTTGTA    3900

CATACTTGCA GTGTACCATC GCTCATGCCT TGGAGAAAAC CAAATACCCC AACTCGGACA    3960

TATACTTGGA CAAATTCGAC AGCCAGTACC ACTTCTCTTG CCAGTTCACA GCTGACCTTA    4020

TTGCCATGAA CCACACCGAT TTCATCATCA CCAGCACATT CCAAGAAATC GCGGGAAGGT    4080

AGAATTTGTA TATTAGTACG CTGTGCTTTA GTAGTAAATA AAACTAGTAT GTGATGTTTT    4140

CTGTGTTGTT TCTGCAGCAA GGACACCGTG GGGCAGTACG AGTCCACAT CGCGTTCACT     4200

CTTCCTGGGC TCTACCGTGT CGTCCATGGC ATCGATGTTT TCGATCCCAA GTTCAACATT    4260

GTCTCCCCTG GAGCAGACAT GAGTGTTTAC TACCCGTATA CGGAAACCGA CAAGAGACTC    4320

ACTGCCTTCC ATCCTGAAAT CGAGGAGCTC ATCTACAGCG ACGTCGAGAA CTCCGAGCAC    4380

AAGTGAGTAT ACTGAAAACT GGTTGCATGT CTTACTGCAG CCAATCAGCT TGTAAATACT    4440

CCAACACCCA TCGCATGATC TATCCATCTT TCTATCTGTC ACCTGAGCTG AACACCTGGT    4500

GTTTACTTGC ATCCAGGTTC GTGCTGAAGG ACAAGAAGAA GCCGATCATC TTCTCGATGG    4560

CGCGTCTCGA CCGCGTGAAG AACATGACAG GCCTGGTCGA GATGTACGGC AAGAACGCGC    4620

GCCTGAGGGA GCTGGCGAAC CTCGTGATCG TTGCCGGTGA CCACGGCAAG GAGTCCAAGG    4680

ACAGGGAGGA GCAGGCGGAG TTCAAGAAGA TGTACAGCCT CATCGACGAG TACAAGTTGA    4740

AGGGCCATAT CCGGTGGATC TCGGCGCAGA TGAACCGCGT CCGCAACGGG GAGCTGTACC    4800

GCTACATTTG CGATACGAAG GGCGCATTCG TGCAGGTATA TGCACACACA CACACACACT    4860

TGGATCTAAT ATCTAACCTC CCAAGTTCCC ACAACGGTGC AATCTACTTT CAGACAACAA    4920

CAGTCACTGA ATCATTTCAT CACTTTGTTT TTTTTTTGTG TGGGTAGCCT GCGTTCTACG    4980

AAGCGTTCGG CCTGACTGTG ATCGAGTCCA TGACGTGCGG TCTGCCAACG ATCGCGACCT    5040

GCCATGGCGG CCCTGCTGAG ATCATCGTGG ACGGGGTATC TGGCCTGCAC ATTGACCCTT    5100

ACCACAGCGA CAAGGCCGCG GATATCCTGG TCAACTTCTT TGACAAATGC AAGGCAGATC    5160

CGAGCTACTG GGACAAGATC TCACAGGACG ACCTGCAGAG AATTTATGAG AAGTATGCAT    5220

TTTTTTTCTC TCCTGCCATA CAATGTAAAA TTCTTGTTGA CTGAAGGCGC ATCTGTTTTA    5280

CTCCCACGGA CACTCGGAAA TCTGCCGTAC CCTTCTCTAG TTAGGAGGAG TAGTAAAAAA    5340
```

```
ATACTGACAC TACAAGCTTT GGATTGCTCA GGTACACCTG GAAGCTCTAC TCCGAGAGGC    5400

TGATGACCCT GACCGGCGTG TACGGGTTCT GGAAGTACGT GAGCAACCTG GAGAGGCGCG    5460

AGACCCGCCG CTACATCGAG ATGTTCTACG CCCTGAAGTA CCGTAGCCTG GTAAGCCGTT    5520

TGATGCCTGC CTCTGCCTCT GCCTCTGCCT GCTAGAGAGG ATCACGTGCT CGTTCCCATT    5580

CCAGCAGTCT TAAACGAGTG GATGAACTAC TGACGCCTCT CTTTCTGGAA TCCAGGCAAG    5640

CCAGGTTCCG CTGTCCTTCG ATTAGTACGG GGAAAGAAGA AGCCCAGGCC GGAGAACCAT    5700

CGCCTGCATT TCGATCTGTT TCACCGCAAT TCGCATTGTT AGTCGTGTAT GGAGTTATG     5760

TGTACTTGGT TTCCAAGAAC TTTGGTTCCT TGTTTTTTTT TCTTTCTTGT TTGAGCGTTT    5820

TTGGGCAGCG CTGGCCTGGT TCCTAGTATG GTGGGAATTG GCTGCACCTT TTGCTTCGAA    5880

TAAAAATGCC TGCTCGTTCA CCTGTCTTCC GGAGTGCAAT GGGATGTTCT GACTGATGGC    5940

GATGTTGTGT TCTTCTGTTA ATCGCCTGTT TAACGTGGTA GGCTGATGCT TGTTCTTGTT    6000

GAGAAAGCTT GCTGTGCCAG ACACTGTCTT GAATACAAGT GAAGAAAAAA AAAAGGCATG    6060

CCAAGTAAAG TTGCACAAAA TTTCCAACTG CTCAGTGGAC CACTGGACCA TGTTCTTGGT    6120

TATAGCAGTT GCAAGGCTTC ACATGGCGTT TGGACAGCAG TCTTGGATTG ATGCATAAAG    6180

AGGTGGTGGT TAACTGAGGA CGCAAGGCCG TTCCCTCAGA GTCAGTCACA AGGTTGCAGA    6240

GCTCACGGTT CTCTTCCCTT TCCGCTTCCT GTCACATCGG AATTGTTGTT TACGCCATCA    6300

GCCCATCACC CACCAAACAC TTAGTTCTAT GTTTCTGTAC TGGATCTTTC AATGCGGAAC    6360

GCGCTTAGTT CCTTCGTGAC AGTCGA                                        6386

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (vi) ORIGINAL SOURCE:
        (A) ORGANISM: Zea mays (xi) SEQUENCE DESCRIPTION: SEQ ID NO:2:

CCGACCATTG GGTATTCTGA ACCATCGACC                                     30

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: double
        (D) TOPOLOGY: Not Relevant (ii) MOLECULE TYPE: DNA (genomic)

(iii) HYPOTHETICAL: NO (xi) SEQUENCE DESCRIPTION: SEQ ID NO:3:

GATCAAGTGC AAAGCTGCGG ACGGATC                                        27

(2) INFORMATION FOR SEQ ID NO:4:

(i) SEQUENCE CHARACTERISTICS:
        (A) LENGTH: 43 base pairs
        (B) TYPE: nucleic acid
```

```
        (C) STRANDEDNESS: double
        (D) TOPOLOGY: Not Relevant (ii) MOLECULE TYPE: other nucleic acid
         (A) DESCRIPTION: /desc = "synthetic polylinker
             sequence"

(iii) HYPOTHETICAL: NO (xi) SEQUENCE DESCRIPTION: SEQ ID NO:4:

GGTACCCGGG GATCCTCTAG AGTCGAGATC CGTCGACCTG CAG                              43
```

MEANS FOR ENHANCING GENE EXPRESSION

RELATED APPLICATIONS

This application is a continuation of U.S. patent application Ser. No. 08/418,540 filed Apr. 7, 1995 now abandoned which is a continuation-in-part of U.S. Ser. No. 08/102,115 filed Aug. 4, 1993, now abandoned which is a continuation of U.S. Ser. No. 07/830,956 filed Feb. 5, 1992, now abandoned, which is a continuation of U.S. Ser. No. 07/353,854 filed May 18, 1989, now abandoned, all incorporated by reference herein.

This invention was made with partial support of U.S. Dept. of Agriculture grants 7223030-12 and 7223041-12. The government has certain rights in this invention.

FIELD OF THE INVENTION

The present invention relates generally to a means for enhancing the expression of a gene. More particularly, the invention relates to a method of enhancing gene expression using the first intron of the shrunken-1 locus of maize.

BACKGROUND OF THE INVENTION

Eukaryotic gene expression is regulated by events at the levels of transcription, post-transcriptional processing, translation and stability of the mature mRNA. The removal of introns from the primary transcript is an essential step, and the use of alternative splicing patterns is one mechanism by which introns participate in the regulation of gene expression. The presence of some introns stimulate genes of mammals and their viruses. (C. J. Lai and G. Khoury (1979) Proc. Natl. Acad. Sci. 76:71–75; D. H. Hamer et al. (1979) Cell 18:1299–1302; P. Gruss and G. Khoury (1980) Nature 286:634–637; C. S. Gasser et al. (1982) Proc. Natl. Acad. Sci. 79:6522–6526; A. R. Buchman and P. Berg (1988) Mol. Cell. Biol. 8:4395–4405; and M. J. Evans and R. C. Scarpula (1989) Gene 84:135–142.) More recently, certain plant introns were shown to increase expression of homologous or heterologous genes in monocot and dicot species (J. Callis et al. (1987) Genes Develop. 1:1183–1200 and E. M. Silva et al. (1988) Genome 30(1):72). The identification and characterization of DNA elements that increase gene expression is essential to optimize expression of introduced genes in host cells, particularly transformed plant cells.

The shrunken-1 (Sh1) locus of maize encodes the major endosperm sucrose synthase, an enzyme important in the synthesis of starch. Loss of this enzymic activity results in inadequate starch levels and, in turn, in shrunken or collapsed kernels at maturity. Because of the gene's importance in starch metabolism, its very abundant transcript, its pivotal role in the study of transposable elements, and the extent of natural variation within the gene, the Sh1 locus has been cloned, its structure elucidated, and DNA sequence determined. (W. Werr et al. (1985) EMBO J. 4:1373–1380; H. Sheldon et al. (1983) Mol. Gen. Genet. 190:421–426; and C. D. Zack et al. (1986) Maydica. 31:5–16.)

The Sh1 locus is large and complex. The gene is composed of 16 exons and is 6 kbp in length. A relatively large intron of over 1000 base pairs separates the first and second exons. Although little is known about the function of such introns, it has been hypothesized that they may function to create new proteins by moving exons and/or changing rates of recombination within genes. (W. Gilbert (1978) Nature 271:501.)

Callis et al. (1987), supra, reported that introns from the maize genes Adh1 and bronze (Bz) increased gene expression in constructs similar to those used in the experiments reported here. Furthermore, Silva et al. (1988), supra, showed that the intron from a heat shock gene of maize increased expression of a reporter gene 3 to 6 fold when the 35S promoter was used to promote transcription.

While several maize introns apparently function to increase gene expression, the extent of activation is quite variable and is also dependent on the sequences being used to promote transcription. Previous studies have shown that the cauliflower mosaic virus 35S (CaMV 35S) promoter is 10–40 fold more effective than the nopaline synthase (NOS) promoter in driving the expression of foreign genes introduced into plant cells (M. Fromm et al. (1985) Proc. Natl. Acad. Sci. USA 82:5824–5828; and R. M. Hauptmann et al. (1987) Plant Cell Rep. 6:265–270). These studies also demonstrated that the CaMV 35S promoter was 10–100 percent less effective in grass cells than in dicotyledonous species such as petunia and carrot. In our attempts to obtain efficient expression of introduced genes, we used promoters of the alcohol dehydrogenase-1 and -2 (Adh1, Adh2) and Sh1genes of maize (R. M. Hauptmann et al. (1988) Plant Physiol. 88:1063–1066). The Adh2 and Sh1 promoters gave no expression in grass protoplasts, while the levels of expression obtained with the Adh1 promoter were approximately 30% of the CaMV 35S promoter.

It has not been possible to predict with certainty which introns will increase expression and under what circumstances. In fact, some studies indicate that certain introns are not involved in gene expression. For example, a 1986 study found that the gene for the seed storage protein phaseolin was expressed at similar levels with or without its introns (P. P. Chee et al. (1986) Gene 41:47–57). Also, Callis et al. (1987), supra, showed that while the Adh1 first intron increased expression 16 to 112 fold when the Adh1 promoter was used, it increased expression only 5 to 22 fold in constructs containing the 35S promoter.

The present invention is based on a detailed analysis of the 5' untranslated region of the Sh1gene which has in part been described by V. Vasil et al. (1989) Plant Physiol. 91:1575–1579, incorporated by reference in its entirety herein.

BRIEF SUMMARY OF THE INVENTION

This invention is based on the discovery that the first intron of the shrunken-1 (Sh1) locus of Zea mays (maize) and adjacent exon sequences stimulate expression of a structural gene when placed in the transcribed but untranslated 5' region of the gene. The maize Sh1 first intron as described herein is useful in the art of genetic engineering to enhance expression of structural genes placed downstream therefrom. The Sh1 first intron is useful, in particular, as a component of a chimeric foreign gene, which can be introduced into a host cell or host tissue where the structural gene is expressed. The invention can be used, for example, to increase expression of genes which have been transformed into plants. As shown herein, the Sh1 first intron increases activity up to 100 fold in otherwise identical constructs and host cells. The Sh1first intron is functional when placed 5' to any structural gene and functions generally in all biological systems, including plants, yeasts, insect cells and mammalian cells.

Functional analysis of the upstream region of the Sh1gene by gene manipulation experiments, including deletion and insertion analyses, demonstrates that DNA sequence suitable for significant stimulation of gene expression is contained in the 5' and 3' splice sites of the Sh1 intron 1 cassette and short sequences flanking them. Increased expression occurs upon insertion of an intron comprising a 5' splice site of the Sh1 first intron and a 3' splice site of the Sh1 first intron, the 5' splice site being situated closer to the 5' end of the gene than the 3' splice site, the intron being inserted between a transcription start site and a translation start site of the gene. Significant expression enhancing capability is associated with the Sh1 intron 1 upstream DNA sequence extending from the 5' splice site between nucleotides 52 and 53 to about nucleotide 178 and from about nucleotide 823 to the 3' splice site between 1080 and 1081 relative to the start of Sh1gene transcription. Deletion of at least the internal two-thirds (649 bp) of the Sh1 first intron results in enhancement of gene expression comparable to the full-length Sh1 intron 1. DNA sequences which affect enhancement of gene expression, as described herein, and which have at least about 80% sequence homology to the functional Sh1 first intron of the present invention as shown in FIG. 1, SEQ ID NO:1 from nucleotide 53 to 1080, are considered to be functionally equivalent thereto. Similarly, DNA sequences which affect enhancement of gene expression and which have at least about 80% sequence homology to the functional fragments of the Sh1 first intron are considered to be functionally equivalent thereto.

Additional expression enhancing capability is associated with the short 5' and 3' flanking regions of the Sh1 intron cassette as shown in FIG. 1, SEQ ID NO:1 from nucleotide 43 to 52 (Sh1 exon 1) and from nucleotide 1081 to 1097 (Sh1 exon 2). DNA sequences which affect enhancement of gene expression, as described herein, and which have at least about 80% sequence homology to the functional flanking regions of the Sh1 first intron of the present invention as shown in FIG. 1, SEQ ID NO:1 from nucleotide 43 to 52 and from nucleotide 1081 to 1097, are considered to be functionally equivalent thereto.

The primary functional elements which confer enhanced expression are the 5' and 3' flanking sequences, which confer significant enhancement of any intron, and sufficient intron sequences to create 5' and 3' splice sites, properly oriented with respect to the direction of translation. Since the majority of sequence within the Sh1 first intron has been shown to be non-essential for enhancement, it follows that the deletable sequence can be replaced by another nucleotide sequence, e.g. randomly generated, provided that internal splice sites are not generated thereby such that the internal splice sites lie in opposite orientation to the normally oriented 5' and 3' splice sites of the intron.

Homologs of the Sh1 first intron and flanking sequences of the present invention may be identified by the ability of their nucleic acids to cross-hybridize under conditions of appropriate stringency as is well understood in the art. It will be understood that there may be minor sequence variations within sequences utilized or disclosed in the present application. A skilled artisan can test allowable variations in sequence, without expense of undue experimentation, by well-known mutagenic techniques which include, but are not limited to, those discussed by D. Shortle et al. (1981) *Ann. Rev. Genet*. 15:265; M. Smith (1985) *Ann. Rev. Genet*. 19:423; D. Botstein and D. Shortle (1985) *Science* 229:1193; by linker scanning mutagenesis (S. McKnight and R. Kingsbury (1982) *Science* 217:316), or by saturation mutagenesis (R. Myers et al. (1986) *Science* 232:613). These variations may be determined by standard techniques in combination with assay methods described herein to enable those in the art to manipulate and bring into utility the various functional units. Using the methods described herein the skilled artisan can without application of undue experimentation test altered sequences within the Sh1 first intron cassette for retention of function. All such shortened or altered functional sequences of the DNA sequences described herein are deemed equivalent thereto and are within the scope of this invention.

It is a principal object of the present invention to provide a method of using the Sh1 first intron and optionally adjacent exon sequences described herein for enhancing expression of a structural gene. This is accomplished by introducing the Sh1 first intron and/or flanking exon sequence, or functional fragments thereof, into a host cell or host tissue by any means known to the art. In one embodiment of the present invention, a plant-expressible gene complex consisting of the Sh1 first intron or a functional fragment thereof, appropriate promoter and other regulatory sequences, and a foreign structural gene is introduced into a plant cell or plant tissue. In an alternative embodiment, a plant-expressible gene complex comprising the exon sequences flanking the Sh1 first intron, or functional equivalents thereof, is introduced into a plant cell or plant tissue. The methods of the present invention are generally applicable to the expression of structural genes in all biological systems, including plants, yeasts, insect cells and mammalian cells.

BRIEF DESCRIPTION OF THE FIGURES

FIGS. 1A–1G (SEQ ID NO:1) show the DNA sequence of the shrunken-1 gene.

FIGS. 7A–7C show the composition of the 5' leader region and sequences of the Sh1 and Adh1 exon fragments. FIG. 7A shows the 5' untranslated region of p35SCN, including the 43 nucleotide polylinker sequence (SEQ ID NO:4) and restriction enzyme sites. Transcription and RNA translation start sites are indicated by +1 and ATG, respectively. FIG. 7B (SEQ ID NO:2) and FIG. 7C (SEQ ID NO:3) show sequences of the Sh1 and Adh1 exon fragments, respectively, which were placed in the polylinker of p35SCN as described hereinbelow and in Table 5.

DETAILED DESCRIPTION OF THE INVENTION

Figure 2:
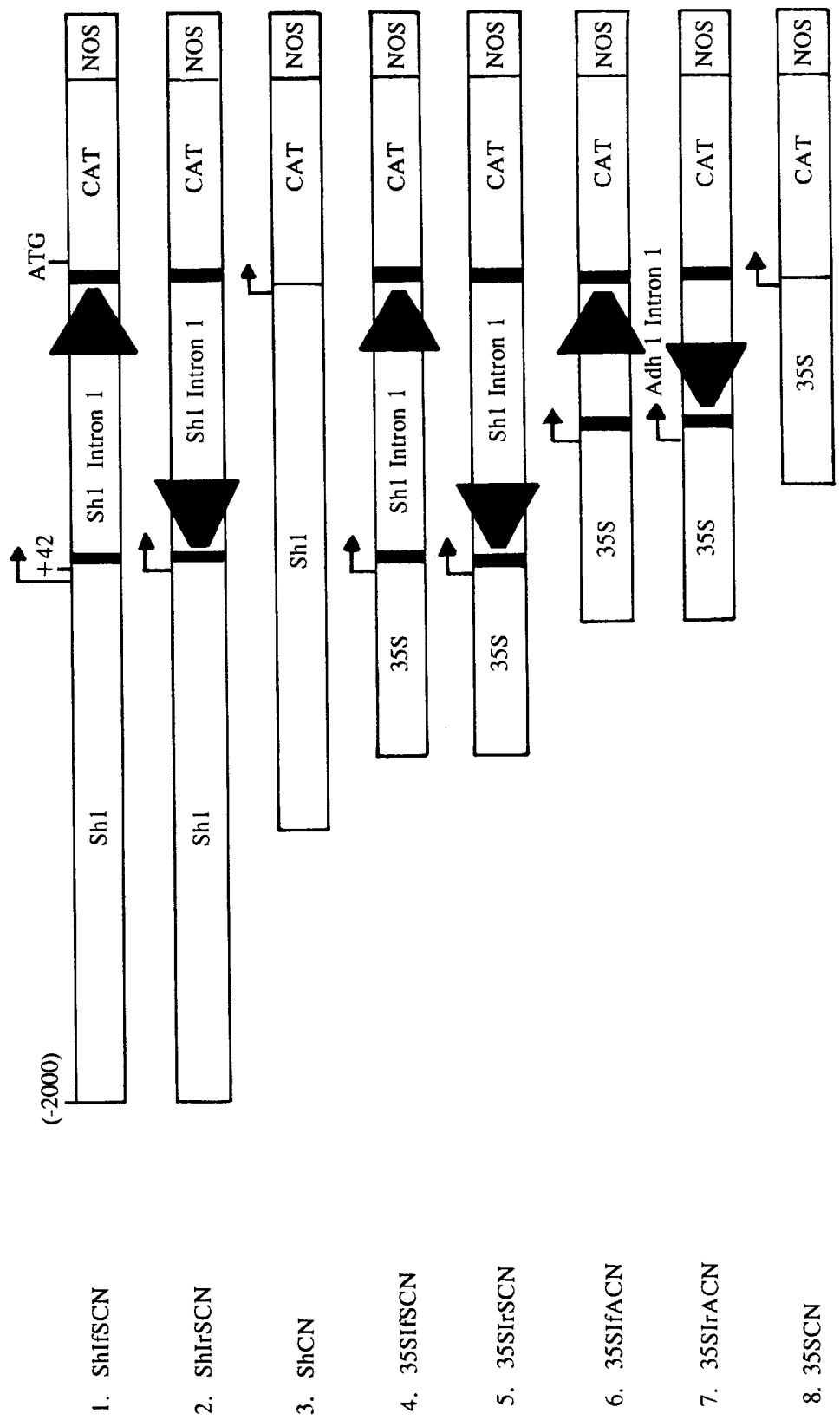
FIG. 2 shows gene constructions used for analysis of intron stimulation of gene expression and comparison of promotor strengths. Maps are drawn to approximate scale and the 2.7 Kb plasmid vector pUC19 is not shown. Nucleotide numbering for the 5' end of the Sh1 promoter is approximate. For each construction, the transcription start site is designated by the bent arrow, the translation initiation site in the CAT coding region is indicated by the ATG (as shown for construction pShIfSCN (line 1)), and the 3' polyadenylation signal is from the nopaline synthase gene. Intron orientation is indicated by the large arrow head and flanking exon sequences are shown as solid boxes. The Sh1 intron 1 cassette contains the complete 1028 bp intron with 10 bp of exon 1 and 17 bp of exon 2 sequence. The Adh1 intron 1 fragment consists of 14 bp exon 1, the 543 bp intron and 5 bp exon 2. No ATG trinucleotide is present in the polylinker or short exon regions flanking the Adh1 intron inserted in either orientation. The inverted Sh1 intron construction pShIrSCN (line 2) contains an ATG in the reversed exon 1 sequence approximately 50 bp 5' to the CAT coding region ATG.

The following definitions are provided to remove any potential ambiguities as to the intent or scope of their usage in the specification and claims.

"Intron" refers to non-coding transcribed sequences which often occur within eukaryotic gene sequences. They can be situated within the coding sequence itself, where they then interrupt the co-linear relationship of the gene with the encoded polypeptide. They may also occur in the 5' or 3' untranslated regions of the gene, but in any event they are present in the gene and primary transcript but absent from mature messenger RNA. The "intron" of the present invention, the first intron of the Sh1 locus of maize, occurs as a non-coding sequence in the 5' untranslated region of the Sh1 locus. The term "Sh1 first intron" refers, herein, to functional DNA sequence identified within the 5' untranslated region of the Sh1 gene of maize. This sequence of DNA acts, in an orientation-dependent fashion, to enhance expression in cells and tissue of any gene into which the intron is inserted as described herein. The Sh1 first intron, described herein, functions to increase expression when positioned between the promoter and coding region of a gene. The activities of various DNA fragments containing the Sh1 first intron or modification thereof have been assessed by their ability to enhance expression of a CAT reporter gene. Other DNA fragments that are functionally equivalent to the first intron of the Sh1 gene can be identified using similar assay, the methods of which are well known and routine in the art. An Sh1 first intron can be isolated from the naturally occurring DNA or can be artificially prepared, for example, by the combination of naturally occurring DNA segments or by chemical synthesis of the functional DNA sequence. As is known in the art, the function of a particular DNA molecule is often correlated with its structure, that is its sequence. In some cases, minor sequence variations have little or no effect on functionality. For purposes of the present work, DNA molecules having at least about 80% DNA homology to the first intron of the Sh1 gene are defined as functionally equivalent thereto. Similarly, DNA molecules or fragments having at least about 80% sequence homology to functional fragments of the Sh1 first intron, particularly the functional extremities of the first intron, are considered to be functionally equivalent thereto.

Significant alterations can be made in the Sh1 first intron without substantially affecting the stimulation of gene expression. Duplications of the entire cassette in either a nested or tandem arrangement as well as substantial modifications in intron length do not significantly affect expression levels. Any nucleotide sequence, e.g. randomly generated, up to about 1080 nucleotides may be inserted into the Sh1 first intron without affecting expression provided, that internal splice sites are not generated thereby such that the internal splice sites lie in opposite orientation to the normally oriented 5' and 3' splice sites of the intron.

"Exon" refers to a portion of a split gene that is included in the transcript of a gene and survives processing of the RNA in the cell nucleus to become part of a spliced messenger of a structural RNA in the cell cytoplasm. The terms "Sh1 exon(s)" and "Sh1 exon region(s)" refer, herein, to functional DNA sequences flanking the first intron of the Sh1 locus of maize. Portions of the Sh1 exons, 1 and 2 described herein, termed the 5' and 3' intron flanking regions, respectively, function to increase expression when positioned between the promoter and coding region of a gene. The flanking regions can be isolated from the naturally occurring DNA or can be artificially prepared. For purposes of the present work, DNA molecules having at least about 80% DNA homology to the 5' and 3' flanking regions (SEQ ID NO:1 from nucleotide 43 to 52 and from nucleotide 1081 to 1097) are defined as functionally equivalent thereto.

The Sh1 first intron "cassette" contains the first intron (1028 bp) of the maize Sh1 and adjacent flanking sequences.

A "recombinant DNA molecule" is one which has been artificially produced from parts derived from heterologous sources, which parts may be naturally occurring or chemically synthesized molecules, and wherein those parts have been joined by ligation or other means known to the art.

An "intron-modified gene" refers to a recombinant DNA molecule comprising a gene having an Sh1 first intron or functional fragment thereof introduced therein.

An "exon-modified gene" refers to a recombinant DNA molecule comprising a gene having the 5' and 3' intron flanking regions of intron 1 or functional equivalents thereof introduced therein.

A "splice site" or "splice junction" is a segment containing a few nucleotides that reside at the ends of introns and function in excision and splicing reactions during the processing of transcripts from split genes. The term "5' splice site" refers, herein, to the sequence at the 5' end of the Sh1 first intron of the present invention. The "5' splice site" of an intron of the present invention is characterized by having at least a "GT" dinucleotide at the 5' end. The term "3' splice site" refers, herein, to the sequence at the 3' end of the Sh1 first intron of the present invention. The "3' splice site" of an intron of the present invention is characterized by having at least an "AG" dinucleotide at the 3' end.

"Expression" refers to the transcription and translation of a structural gene so that a protein or polypeptide is made. Gene expression can be assessed by direct detection of protein product, detection of the mRNA products of transcription, by protein gel-electrophoresis or immunological methods, for example.

"Promoter" refers to sequences at the 5'-end of a structural gene which direct the initiation of transcription. Promoter sequences are necessary, but not always sufficient, to drive expression of the downstream structural genes. The promoter itself may be a composite of segments derived from more than one source, naturally occurring or synthetic.

"Plant-expressible gene" refers to the combination of a structural gene and the regulatory DNA sequences necessary to allow expression of that structural gene in a plant cell or tissue. A plant-expressible gene may be composed of a structural gene and its homologous regulatory sequences including a promoter or be a chimeric construction composed of regulatory sequence and a structural gene coding sequence from different gene sources. The terms "structural gene" and "coding region" refer to that portion of a gene comprising a DNA segment coding for a protein, polypeptide or portion thereof, possibly including a ribosome binding site and/or a translational start codon. The terms can also refer to copies of a structural gene naturally found within the cell, but artificially introduced. In this case, the structural gene naturally occurring in a cell may be reintroduced into a cell as part of a chimeric gene having non-natural regulatory control sequences, for example under the control of the Sh1 first intron or adjacent flanking sequences. The structural gene may encode a protein not normally found in the cell in which the gene is introduced, in which case it is termed a foreign structural gene. A foreign structural gene may be derived in whole or part from a bacterial genome or episome, eukaryotic nuclear or plastid DNA, cDNA, viral DNA, or chemically synthesized DNA. It is further contemplated that a structural gene may contain one or more modifications in either the coding segments or in the untranslated regions which could affect the biological activity or the chemical structure of the expression product, the rate of expression or the manner of expression control. Such modifications include, but are not limited to, mutations, insertions, deletions, and substitutions of one or more nucleotides. The structural gene may be a composite of segments derived from a plurality of sources, naturally occurring or synthetic. The structural gene may also produce a fusion protein. For eukaryotic systems, a structural gene is considered to include a polyadenylation signal downstream from the translation termination codon. The polyadenylation signal sequence may be that of the structural gene employed or obtained from another source, including for example a chemically synthesized DNA sequence. The polyadenylation signal effects mRNA processing, usually by the addition of polyadenylatic acid tracts to the 3'-ends of the precursor mRNAs. It is known that a canonical polyadenylation signal may cause a cleavage of the transcript and not polyadenylation per se (C. Montell et al. (1983) Nature 305:600). It is contemplated that the introduction of recombinant DNA molecules containing the promoter/Sh1 first intron and/or flanking exons/structural gene/polyadenylation signal expression complex will include constructions wherein any or all of the component parts are not derived from the same gene source.

As used herein, "plant tissue" includes differentiated and undifferentiated tissues of plants including, but not limited to, roots, shoots, leaves, pollen, seeds, tumor tissue, such as crown galls, and various forms of aggregations of plant cells in culture, such as embryos and calli.

The term "chemically synthesized," as related to a sequence of DNA, means that the component nucleotides were assembled in vitro using nonenzymatic means. Manual chemical synthesis of DNA may be accomplished using well established procedures (e.g., M. Caruthers (1983) in Methodology of DNA and RNA Sequencing, Weissman (ed.), Praeger Publishers (New York) Chapter 1) or automated synthesis can be performed using one of a number of commercially available machines.

"Regulatory control" refers to the modulation of gene expression by sequence elements positioned appropriately with respect to the transcription initiation site of the gene. This term refers to the positioning of promoter regions and other regulatory sequences, i.e. those responding to stimuli, most often, upstream of the genes which they regulate. Regulation may result in an on/off switch for transcription, or it may result in variations in the levels of gene expression. To place a gene under regulatory control of sequence elements means to place it sufficiently close to such sequence elements so that the gene is switched on or off, or its level of expression is measurably varied, as is understood by those skilled in the art. In this invention, the Sh1 first intron and flanking sequences increase the level of expression up to 100 fold. The Sh1 first intron sequences of the present invention function when placed between the transcription start site and the translation initiation site.

"Homology" as used herein refers to identity of nucleotide sequences. The extent of homology between DNA sequences can be ascertained by direct sequencing or can be empirically determined in DNA hybridization experiments, such as those described in B. D. Hames and S. J. Higgins (1985) Nucleic Acid Hybridization, IRL Press, Oxford UK.

The subject invention concerns the discovery that the first intron of the shrunken-1 locus of maize significantly enhances expression of a reporter gene when transcription is driven by the CaMV 35S promoter or by the homologous Sh1 promoter. Enhanced expression occurs in protoplasts of each of three different grass species analyzed although our data suggest that the maize intron is particularly active in maize protoplasts. Because the increased expression is dependent upon the orientation of the intron relative to the rest of the construct, normal intron processing apparently is required for increased gene expression.

The Sh1 first intron is particularly useful for enhancing expression of introduced foreign genes. The subject invention can be used to increase gene expression where a potentially selectable gene is normally expressed at suboptimal levels. Enhanced gene expression via the Sh1 first intron is especially useful when an inserted gene codes for an agriculturally important trait.

Although the use of the intron of the subject invention to enhance expression in certain plant species is specifically exemplified herein, the methods of the present invention are also useful for enhancing expression in other systems, including yeasts, insect cells, and mammalian cells.

The Sh1 locus contains a 1028 bp intron which separates exon 1 and exon 2. The DNA sequence for Sh1 is shown in FIG. 1 (SEQ ID NO:1). While the original evidence for the existence of this large first intron was based on primer extension and S1 protection data, subsequent isolation and sequencing of an almost full length cDNA clone has provided definitive evidence for the existence of this intron. Analysis of the CDNA sequence strongly supports S1 protection data and indicates that the start of translation occurs in the second exon. Thus the very large first intron does not separate protein-coding information. If one accepts the premise that introns were used in evolution to bring together functional polypeptide domains into different proteins (e.g., W. Gilbert (1978) *Nature* 271:501 and W. Gilbert (1985) *Science* 228:823–824) or that introns provide recombinational length to genes in order to create unique coding information from preexisting alleles, then one would not expect introns to fall in nonprotein-coding exon sequences. The finding that the first intron of Sh1 greatly increases gene expression, therefore, provides an explanation for the existence of such an intron.

The first intron and/or adjacent sequences of the shrunken-1 locus of maize can be incorporated into constructs containing a protein-coding sequence, for example, the chloramphenicol acetyltransferase gene (CAT) coupled with the nopaline synthase 3' polyadenylation signal. Transcription can be driven with any appropriate promoter, for example, the 35S promoter of the cauliflower mosaic virus (CaMV) or the Sh1 promoter of maize, both exemplified herein. In experiments where transient gene expression was monitored following electroporation into protoplasts of *Panicum maximum* (Guineagrass), *Pennisetum purpureum* (Napiergrass) or *Zea mays* (maize), the Sh1 intron increased gene expression in cells of each species; 5 to 91-fold increases were observed. Expression levels observed in maize were 2 and 8 times those observed in Napiergrass and Guineagrass, respectively. The 35S promoter gave CAT activity 10 to 100 times that observed with the Sh1 promoter.

In similar constructs, the first intron of the alcohol dehydrogenase-1 (Adh1) gene of maize led to increased gene expression of only 7–10% of that observed with the Sh1 first intron. Thus, the Sh1 first intron appears to be the most effective among analyzed plant introns in increasing gene activity.

Elevated levels of gene expression are seen only when the cassette resides in the transcribed but untranslated 5' region of the gene. Gene expression was reduced by placement of the Sh1 intron 1 cassette in the 3' untranslated region upstream of the polyadenylation region. This decrease could be due to inaccurate or inefficient splicing per se, or the impact of reduced spliceability on polyadenylation efficiency. Interestingly, the relative positions of splicing and polyadenylation signals influence alternative processing of transcripts.

Significant alterations can be made in the Sh1 intron 1 cassette without substantially affecting the stimulation of gene expression. Duplications of the entire cassette in either a nested or tandem arrangement as well as substantial modifications in intron length did not significantly alter the increase of CAT activity. Collectively, the data show that only the 5' and 3' extremities of the Sh1 intron 1 cassette are essential for high levels of gene expression enhancement. Orientation of sequences within the intron must be compatible with the enhancement mechanism, however, since the placement of inverted Sh1 sequences in this region abolished the stimulatory effect.

Surprisingly, the approximately 30 bp of Sh1 exon and linker sequences that flank the intron in the Sh1 cassette enhance gene expression independently of the intron. The flanking region of the Sh1 intron 1 cassette boosts gene expression approximately 7 fold in the absence of the intron, while exon sequences from the Adh1 gene inhibit gene expression. Placement of the Adh1 exon sequence adjacent to the Sh1 first intron, however, elevates gene expression above the level observed with the Sh1 first intron cassette. These mixing experiments strongly suggest that the exon and intron components of the Sh1 first intron cassette act at different steps in gene expression.

As shown by exon swapping experiments, the magnitude of intron-mediated enhancement correlates with relative fit to consensus splice site sequences. Expression levels of the hybrid exon/intron/exon cassettes reflect their predicted splicing efficiencies. The independent effect of the Sh1 exon region is apparently sequence-specific, influenced by surrounding sequences, and is possibly at the level of translational efficiency or message stability.

The transcribed portion of the Sh1 gene of maize thus contains at least three elements which act independently to increase gene expression. The first intron and the exon sequences abutting it each function to increase gene expression.

The recombinant DNA molecule carrying the desired structural gene under the control of promoter sequences and the Sh1 first intron (intron-modified gene) or exons (exon-modified gene) can be introduced into host cells or tissue by means known to the art. The technique used for a given host species or specific type of host tissue depends on the known successful techniques. As exemplified herein, foreign DNA sequences can be introduced into plant tissue by electroporation (M. Fromm et al. (1985) *Proc. Natl. Acad. Sci. USA* 82:5824). Alternative means for introducing recombinant DNA into plant tissue include, but are not limited to, direct protoplast transformation with DNA (J. Paszkowski et al. (1984) *EMBO J.* 3:2717), microinjection (A. Crossway et al. (1986) *Mol. Gen. Genet.* 202:179), ballistic transformation using microscopic particles coated with DNA (D. T. Tomes et al. (1990) *Plant Mol. Biol. Manual* A13:1–22), and T-DNA mediated transfer from *Agrobacterium tumefaciens* to the plant tissue. There appears to be no fundamental limitation of T-DNA transformation to the natural plant host range of Agrobacterium. Successful T-DNA mediated transformation of monocots (G. M. S. Hooykaas-Van Slogteren et al. (1984) *Nature* 311:763–764), gymnosperms (A. M. Dandekar et al. (1987) *Biotechnol.* 5:5897–5900) and algae (R. L. Ausich EPO Publication No. 108,580) has been reported. Representative T-DNA vector systems are described in the following references: G. An. et al. (1985) *EMBO J.* 4:277; L. Herrera-Estrella et al. (1983) *Nature* 303:209; L. Herrera-Estrella et al. (1983) *EMBO J.* 2:987; L. Herrera-Estrella et al. (1985) in Plant Genetic Engineering, New York: Cabridge University Press, p.63).

Once introduced into the plant tissue, the expression of the structural gene may be assayed by any means known to the art, and expression may be measured at the transcriptional level or as protein synthesized. Techniques are known for the in vitro culture of plant tissue, and in a number of cases, for regeneration into whole plants. Procedures for transferring the introduced expression complex to commercially useful cultivars are known to those skilled in the art. Plant tissue transformed to contain the DNA molecules of the present invention can be identified by the presence of the DNA sequences introduced, for example, using DNA hybridization assays. The presence of the introduced DNA fragments is an identifiable phenotype of the transformed tissue.

As novel means are developed for the stable insertion of foreign genes into plant cells and tissue and for manipulating transformed cells and tissue to obtain transformed plants, those of ordinary skill in the art will be able to employ the DNA fragments and constructs of the present invention in combination with any such desired novel means without exercise of undue experimentation.

The following examples are provided for illustrative purposes only and are not intended to limit the scope of the invention. The examples utilize many techniques well known and accessible to those skilled in the arts of molecular biology and in the manipulation of recombinant DNA in plant tissue. Enzymes are obtained from commercial sources and are used according to the vendors' recommendations or other variations known in the art. Reagents, buffers and culture conditions are also known to the art. References containing standard molecular biological procedures include T. Maniatis et al. (1982) Molecular Cloning, Cold Spring Harbor Laboratory, Cold Spring Harbor, N.Y.; R. Wu (ed.) (1979) Meth. Enzymol. 68; R. Wu et al. (eds.) (1983) Meth. Enzymol. 100 and 110; L. Grossman and K. Moldave (eds.) (1980) Meth. Enzymol. 65; J. Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley, Calif.; R. Schlief and P. Wensink (1982) *Practical Methods in Molecular Biology*; Glover (ed.)(1985) *DNA Cloning*, Vols. I and II, IRL Press, Oxford, UK; Hames and Higgins (eds.) (1985) *Nucleic Acid Hybridization*, IRL Press, Oxford, UK; Setlow and A. Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein.

EXAMPLES

Example 1

Cell Lines, Protoplast Isolation and Electroporation

Protoplasts were isolated from cell suspension cultures of *Panicum maximum* Jacq. (Guineagrass), *Pennisetum purpureum* Schum. (Napiergrass) and *Zea mays* L. (maize). Guineagrass protoplasts were isolated from cell line Pm85 as previously described (Vasil, V., et al. (1988) *Pl Cell Rep.* 7:499–503). Napiergrass protoplasts were isolated from cell line Pp86 five days following subculture. The maize cell line Mpp was established from protoplast-derived callus of *Zea mays* Dekalb XL82 (Vasil, V. and I. K. Vasil (1987) *Theor. Appl Genet*. 73:793–798), maintained on a 4–5 day subculture schedule, and used for protoplast isolation 3 days after subculture.

The basic cell wall digesting enzyme solution contained 1% Cellulase Onozuka RS (Yakult Honsha) and 1% Pectinase (Serva). In addition, 0.4% Macerozyme R10 (Yakult Honsha) was added for Napiergrass and 0.1% Pectolyase Y23 (Seishin) for maize. The enzymes were dissolved in MES buffer (Vasil, V., et al. (1988) *Pl. Cell Rep*. 7:449–502). Settled suspension culture cells (4–6 ml, 1.2–1.6 gm fresh weight) were dispersed in 50 ml of enzyme and incubated on a gyrorotary shaker (50–60 rpm) for 4–5 hr at room temperature. The protoplasts were sieved, washed three times and counted as previously described (Vasil, V. and I. K. Vasil (1980) *Theor. Gen. Genet*. 56:97–99). Protoplast density was adjusted to $4$–$5\times10^6$/ml. The same number of protoplasts was used in experiments comparing the two promoters and the effect of the inserted introns.

Twenty $\mu$l of plasmid DNA (concentration of each plasmid construct was determined spectrophotometrically and adjusted to 1 $\mu$g/ml with sterile TE) was added to 1 ml of protoplasts at room temperature. Electroporation was done over ice using a BRL Cell Porator with a single pulse of 200 V and capacitance of 1180 $\mu$F. Protoplasts electroporated without plasmid DNA served as negative controls. Electroporated protoplasts were cultured according to methods described by Vasil and Vasil (1988).

All experiments were repeated at least once and each treatment had at least one replicate sample within the same experiment. In order to accurately compare the level of gene expression between different plasmid constructs in one experiment, protoplasts from a single batch were used.

Example 2

DNA Constructs

DNA manipulations were performed using conventional protocols (e.g., Maniatis, T., et al. (1982) Molecular Cloning: A Laboratory Manual (Cold Spring Harbor Laboratory Press). The reporter sequence consisted of the chloramphenicol acetyltransferase (CAT) coding region and nopaline synthase (NOS) 3' polyadenylation signal (Rogers, et al. (1987) *Methods Enzymol.* 153:253–277). The Sh1 promoter fragment has been previously described (Hauptmann, R. M., et al. (1988) *Plant Phys*. 88:1063–1066). The promoter, 5' flanking region, transcription start site, and 5' untranslated leader sequences to +42 in exon 1 (Werr et al. (1985)) were contained in the approximately 2 kb HincII fragment of the Sh1 clone. A modified CaMV 35S promoter containing a duplicated enhancer region was utilized. Construction of this modified 35S promoter was similar to one described elsewhere (Kay et al. (1987) *Science* 236:1299–11302).

The basic plasmid construction p35SCN contained a modified CaMV 35S promoter, the CAT coding region and NOS 3' polyadenylation signal (Vasil, V., et al. (1989) *Plant Physiol*. 91:1575–1579). All gene constructions were cloned in the *Escherichia coli* plasmid vector pUC19. Correct joining, orientation, and sequence of the gene elements were confirmed by restriction analysis, where definitive, and usually by restriction analysis followed by double-stranded DNA sequencing.

The Sh1 first intron with adjacent exon sequences was isolated from the genomic clone p17.6 (Zack, C. D., et al. (1986) *Maydica* 31:5–16) as a HincII/TaqI fragment and subcloned in pUC19/SmaI/AccI. The Sh1 sequences were excised from pUC19 with KpnI and PstI and protruding ends removed by T4 DNA polymerase. The resulting Sh1 intron cassette contains a CC dinucleotide derived from the subcloning at the 5' end, 10 bp of exon 1, the 1028 bp intron, 17 bp of exon 2 and an additional C nucleotide at the 3' end.

The Sh1 intron cassette was inserted in both orientations at the HincII site in the 5' untranslated region between the 35S promoter and the CAT/NOS reporter sequences in p35SCN, to give p35SIfSCN and p35SIrSCN (Vasil, V., et al. (1989)). Additional placement constructions contained the Sh1 intron 1 cassette in each orientation at EcoR1 and HindIII restriction sites shown in FIG. 3A. Restriction sites were rendered blunt-ended with Klenow and the intron cassette cloned 5' to the 35S promoter, at the CAT/NOS junction, and 3' to the NOS polyadenylation region.

The Sh1 intron cassette was cloned into p35SIfSCN at the BamHl site made blunt-ended by Klenow to produce a gene construction containing two tandem copies of the intron cassette each in the 5'→3' orientation. An augmented Sh1 intron construction was produced by cloning an 897 bp internal fragment of the intron into a T4 DNA polymerase blunt-ended SstI site inside the Sh1 intron in p35SIfSCN, with all Sh1 sequences in the 5'→3' orientation. Furthermore, cloning of the complete Sh1 intron cassette at this blunt-ended SstI site produced two gene constructions containing the nested cassette in the normal 5'→3' or the inverted 3'→5' orientation.

Figure 6:
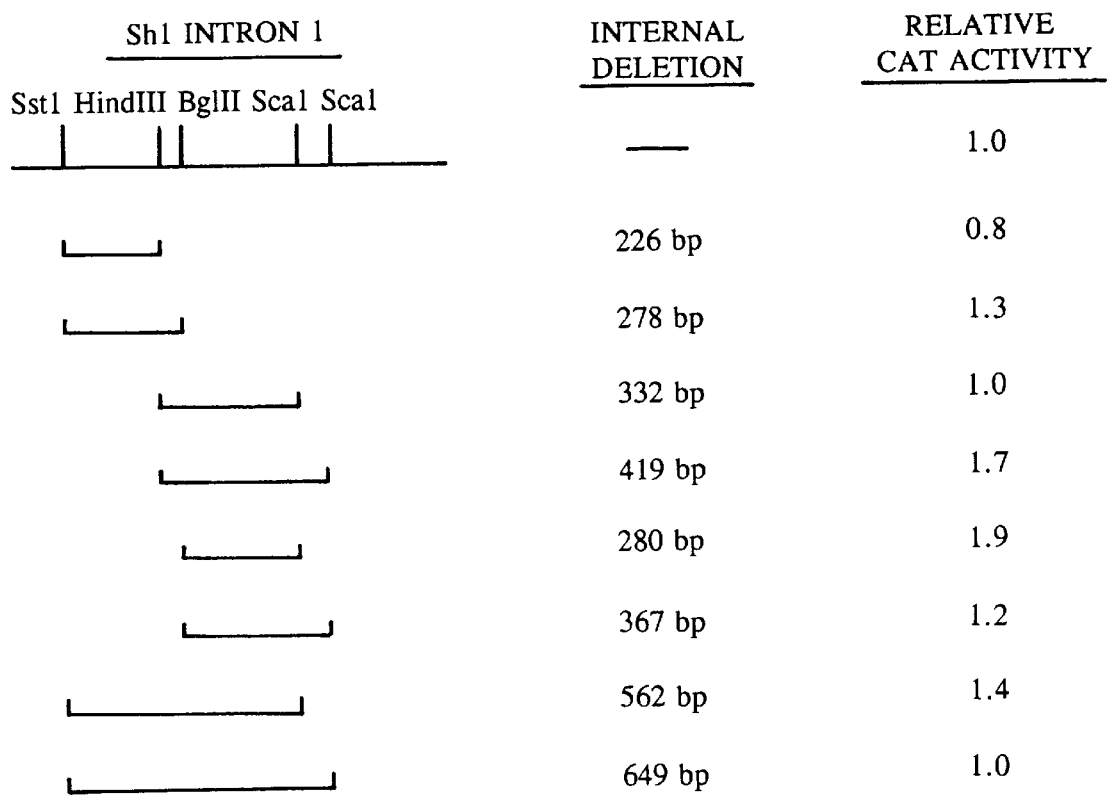
FIG. 6 shows the effect of deletions within the Sh1 intron 1 on transient CAT expression. Deletions within the intron of the Sh1 intron 1 cassette are diagrammed in the first column; column 2 shows the size of each deletion in base pairs (bp). CAT activities are shown relative to the complete Sh1 intron 1 cassette in p35SIfSCN and values are the averages of results from two electroporation experiments with duplicate electroporations and CAT assays within each experiment. The following values indicate the relative CAT activities for each intron deletion construct in the two experiments: 226 bp (0.7, 1.0); 278 bp (1.0, 1.6); 332 bp (0.7, 1.3); 419 bp (1.6, 1.7); 280 bp (2.1, 1.8); 367 bp (0.9, 1.5); 562 bp (1.3, 1.6); and 649 bp (0.9, 1.1).

Internal deletions of the Sh1 intron in p35SIfSCN were created by sequential digestions with combinations of the enzymes SstI, HindIII, BglII and ScaI. Eight constructions with overlapping intron deletions of from 226 bp to 649 bp were generated (FIG. 6).

Sh1 sequences from exons 1 and 2 were isolated as a 25 bp HincII/TaqI fragment of the cDNA clone pC111 (McCarty, Shaw and Hannah, unpublished). The exon sequences fragment was cloned into p35SCN in the 5' untranslated region between the promoter and CAT/NOS in three ways. First, the exon sequences were cloned between the blunt-ended BamHI site and the cohesive AccI site. This produced a gene construction containing 10 bp exon 1 and 17 bp exon 2 in an altered polylinker environment surrounding the insertion as compared to the placement of the Sh1 intron cassette in p35SIfSCN. Secondly, the 25 bp HincII/TaqI fragment was blunt-ended with Klenow and inserted at the HincII site in p35SCN. This yielded a construction containing bp of exon 1 and 15 bp of exon 2 cloned at the same site as the Sh1 intron cassette in p35SIfSCN. Finally, the exon sequences fragment was first subcloned into pUC19 then excised and placed in p35SCN exactly as done for the cloning of the Sh1 intron cassette. The resulting gene construction is identical to p35SIfSCN with respect to its exon sequences (10 bp exon 1, 17 bp exon 2), the additional CC dinucleotide 5' and single C 3', and placement in the polylinker.

The first intron of Adh1 has been described (Dennis, E. S., et al. (1984) *Nucl. Acids Res.* 12:3983–400) and examined for its effect on gene expression (Callis, J., et al. (1987) *Genes Develop.* 1:1183–1200). The plasmid clone pI$_1$[911] was generously provided by M. Fromm. The 534 bp Adh1 intron with short flanking exon and linker sequences was excised with BclI and BamHI and cloned at the BamHI site in p35SCN, producing the construction p35SIfACN (Vasil, V., et al. (1989)). Splicing of the intron using Adh1 splice signals would leave 23 nt inserted in the 5' untranslated region. The Adh1 exon sequences examined by Callis et al. (1987) were synthesized as 23-mer oligonucleotides, kinased and annealed. The resultant double-stranded oligomer contained 14 nt exon 1, 6 nt exon 2, and 7 nt 3' linker, with cohesive 5' BclI and 3' BamHI sites. This Adh1 exon sequences fragment was cloned at the compatible cohesive BamHI site in the 5' untranslated region of p35SCN, generating a 23 bp insertion, or end-filled with Klenow and cloned at the HincII site, resulting in a 27 bp insertion.

Cassettes with hybrid exon/intron/exon sequences were generated using the PCR. Each pair of hybrid PCR primers contained linker and exon sequences from Adh1 coupled to Sh1 intron 1 sequences, or linker and Sh1 exon sequences combined with Adh1 intron 1 sequences. The exon and linker sequences were exactly as described above for the Sh1 intron cassette and the Adh1 intron cassette. These oligonucleotide pairs were used to prime the synthesis of hybrid DNAs from cloned Adh1 and Sh1 intron 1 templates. The correctly sized PCR products were excised from agarose gels, kinased, 3' end-filled with Klenow and cloned at the HincII site in the 5' untranslated region of p35SCN. Final constructions were sequenced to confirm hybrid regions and to exclude mutational events that were generated in the PCR amplifications.

Example 3

Determination of CAT Activity

Approximately 48 hr after electroporation, protoplasts/cells were collected by centrifugation and frozen at −70° C. Total cellular protein was determined by the Bio-Rad Protein Assay and equal amounts of protein were generally used within a single experiment. To keep the CAT assay in the range of enzyme activity where no di-acetylated product was formed, it was necessary to use lower amounts of protein in the assays of some maize cell extracts. A nonlinear correction factor determined from a CAT activity standard curve of protein amounts assayed was used to adjust CAT activities for the other cell extracts in the same experiment. CAT activity was determined from protoplast/cell extracts (heated at 60° C. for 10 min to inactivate any plant-derived background) according to Gorman, C. M., et al. (1982) *Mol. Cell Biol.* 2:1044–1051, using $^{14}$C chloramphenicol (0.3 $\mu$Ci; Amersham) and Acetyl-CoA (20 $\mu$l from a solution of 10 mg/ml; Sigma) as substrates. Radioactive spots of chloramphenicol and its monoacetylated products were visualized from the TLC plates by autoradiography (X-ray film exposed 24 hr) and guantitated by liquid scintillation counting to determine the percentage of acetylated chloramphenicol. Correction for background was made by counting a scraped area of the TLC plate showing no signal on the autoradiograph. CAT activity is expressed as the percentage of acetylated chloramphenicol.

Example 4

Effect of Sh1 Intron on Gene Expression

Two promoters, Sh1 of maize and cauliflower mosaic virus 35S, were monitored for their ability to promote transcription of the CAT gene. All plasmid constructs contained the chloramphenicol acetyltransferase gene coupled to the nopaline synthase 3' polyadenylation signal. In addition, the first intron of the Sh1 locus and of the Adh1 locus of maize were incorporated into the constructs between the promoter and the CAT coding region to determine if the expression of the CAT gene could be increased.

The plasmid constructs used are given in FIG. 2. Cell suspensions of *Panicum maximum* were electroporated with constructs 1 through 5 and 8 of FIG. 2. CAT activity was detected with all constructs except pShIrSCN and p35SIrSCN. These constructs contain the Sh1 first intron in the opposite orientation relative to the direction of transcription.

Data from these experiments are presented in Table 1. Where no intron was present the construct with the CaMV 35S promoter (p35SCN) gave 16 to 29 fold more CAT activity than did the construct with Sh1 promoter (pShCN). CAT activity was increased several fold when the Sh1 first intron was fused to the Sh1 or the CaMV 35S promoter (pShIfSCN, p35SIfSCN). A 5 to 58-fold increase in CAT activity was seen with pShIfSCN relative to its control plasmid pShCN. With the CaMV 35S promoter and the Sh1 first intron (p35SIfSCN), CAT activity was increased 23 to 28 fold relative to the construct without the Sh1 intron (p35SCN). The increase in the expression of CAT was more consistent when transcription was driven by the CaMV 35S promoter (p35SIfSCN) in comparison to the Sh1 promoter (pShIfSCN). This pattern of variable expression by the Sh1 promoter was also exhibited in the other grass species.

TABLE 1

Effect of Intron on Gene Expression When Used With Different Promoters in *Panicum maximum*

| Designation of Construct | Promoter | Intron | CAT Activity (%) Trial 1 | Trial 2 |
|---|---|---|---|---|
| pShCN | Sh1 | none | 0.09 | 0.17 |
| pShIfSCN | Sh1 | Sh1 | 5.44 | 0.92 |
| improvement with intron | | | 57.96x | 5.47x |
| p35SCN | 35S | none | 2.75 | 2.71 |
| p35SIfSCN | 35S | Sh1 | 62.49 | 74.7 |
| improvement with intron | | | 22.7x | 27.55x |

Example 5

Effect of Sh1 Intron on Gene Expression in *Pennisetum purpureum*

We also investigated whether the elevated gene expression caused by the Sh1 first intron occurred in other grass species. Protoplasts isolated from a cell suspension culture of *Pennisetum purpureum* were electroporated with the plasmid constructions. Data from this experiment are shown in Table 2. Elevated levels of CAT activity were obtained with plasmid constructs containing the Sh1 intron 1 (pShIfSCN, p35SIfSCN). A nearly 12-fold increase was observed with the 35S promoter.

TABLE 2

Effect of Sh1 Intron on Gene Expression When Used With Different Promoters in *Pennisetum purpureum*

| Designation of Construct | Promoter | Intron | CAT Activity (%) |
|---|---|---|---|
| pShCN | Sh1 | none | 0.4269 |
| pShIfSCN | Sh1 | Sh1 | 0.8281 |
| improvement with intron | | | 1.94x |
| p35SCN | 35S | none | 4.428 |
| p35SIfSCN | 35S | Sh1 | 50.09 |
| improvement with intron | | | 11.50x |

Example 6

Effect of Sh1 Intron on Gene Expression in *Zea mays*

The ability of the Sh1 first intron to elevate gene expression was also examined in maize protoplasts. The results of these experiments are presented in Table 3. The Sh1 first intron led to a 31 to 91-fold increase when transcription was driven by the 35S promoter, but gene expression was quite variable (1 to 172 times that observed without the intron) when transcription was driven by the Sh1 promoter. As was the case with the other two grass species, the level of expression with the 35S promoter was much higher (16 to 100 fold) than that observed with the Sh1 promoter.

TABLE 3

Effect of Sh1 Intron on Gene Expression When Used With Different Promoters in *Zea mays*

| Designation of Construct | Promoter | Intron | CAT Activity (%) Trial 1 | Trial 2 |
|---|---|---|---|---|
| pShCN | Sh1 | none | 0.0534 | 0.0049 |
| pShIfSCN | Sh1 | Sh1 | 0.0564 | 0.7739 |
| improvement with intron | | | 1.06x | 172.2x |
| p35SCN | 35S | none | 0.8814 | 0.4635 |
| p35SIfSCN | 35S | Sh1 | 27.30 | 42.90 |
| improvement with intron | | | 30.79x | 90.60x |

Example 7

Effect of Intron Orientation on Gene Expression in *Zea mays*

Because previous work showed that the first intron of Adh-1 increased gene activity (Callis et al. 1987), we synthesized 35S-CAT constructs containing this intron in both orientations (entries 6 and 7, FIG. 2). Results from transformation and expression in maize cells are summarized in Table 4. Neither intron stimulated CAT expression when cloned in the reverse orientation. The construct with the Adh1 intron 1 in the correct orientation (p35SIfACN) showed a 3.7-fold increase (average of two experiments) in comparison to 42.8-fold increase by the Sh1 intron (p35SIfSCN) relative to the construct lacking the intron (p35SCN). It can be concluded, therefore, that in the maize protoplasts used in these experiments the Sh1 intron 1 is at least ten times more effective than the Adh-1 intron 1 in stimulating CAT expression.

TABLE 4

| Designation of Construct | Promoter | Intron | Trial | CAT % | Activity Relative to p35SCN |
|---|---|---|---|---|---|
| p35SCN | 35S | none | 1 | 1.46 | 1.0 |
| | | | 2 | 0.58 | 1.0 |
| p35SIfSCN | 35S | Sh1 | 1 | 51.9 | 35.5 |
| | | | 2 | 29.3 | 50.2 |
| p35SIfACN | 35S | Adh1 | 1 | 5.7 | 3.9 |
| | | | 2 | 2.1 | 3.6 |

Example 8

Effect of Placement of the Sh1 Intron Cassette on Gene Expression

DNA constructions, protoplast isolation and electroporation were conducted as described above and in Clancy, M., et al. (1994) *Plant Sci.* 98:151–161, incorporated by reference in its entirety herein. The total cellular protein and CAT activity were determined as previously described.

Electroporations and CAT assays were performed in duplicate for each test of a plasmid construct with a given protoplast preparation. The average SE for duplicate CAT assays from the same protoplast batch was 28% of the mean for 83 pairs of assays. This reflects the average 1.6-fold variation for duplicate assays. We found an average 2.6-fold variation in absolute activities between protoplast preparations. Since both absolute and relative activities vary with protoplast preparations, sets of related plasmid constructs were tested together using the same batch of protoplasts. Data are presented as mean relative activities of at least two experiments.

Figure 3A:
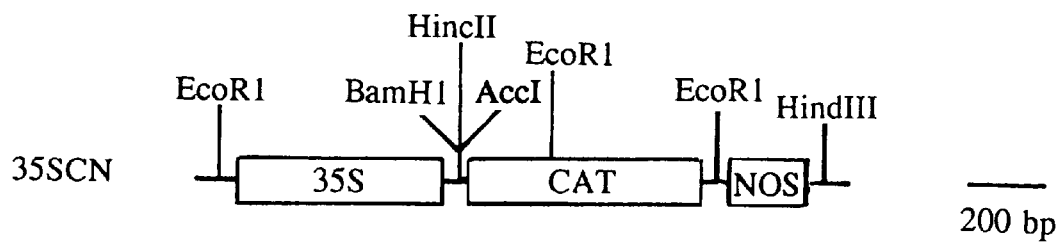
FIG. 3A shows the structure of the basic chimeric gene construction p35SCN. Restriction sites shown are those used for insertion of maize sequences. Gene elements are drawn approximately to scale, and the pUC19 portion of the plasmid is not shown.
Figure 3B:
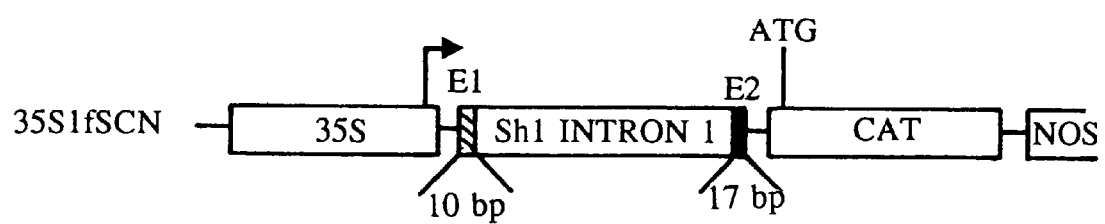
FIG. 3B shows the p35SIfSCN gene construction containing the Sh1 intron 1 cassette cloned at the HincII site of p35SCN. The transcription start site is designated by the bent arrow. The ATG corresponds to the start of translation.
Figure 4:
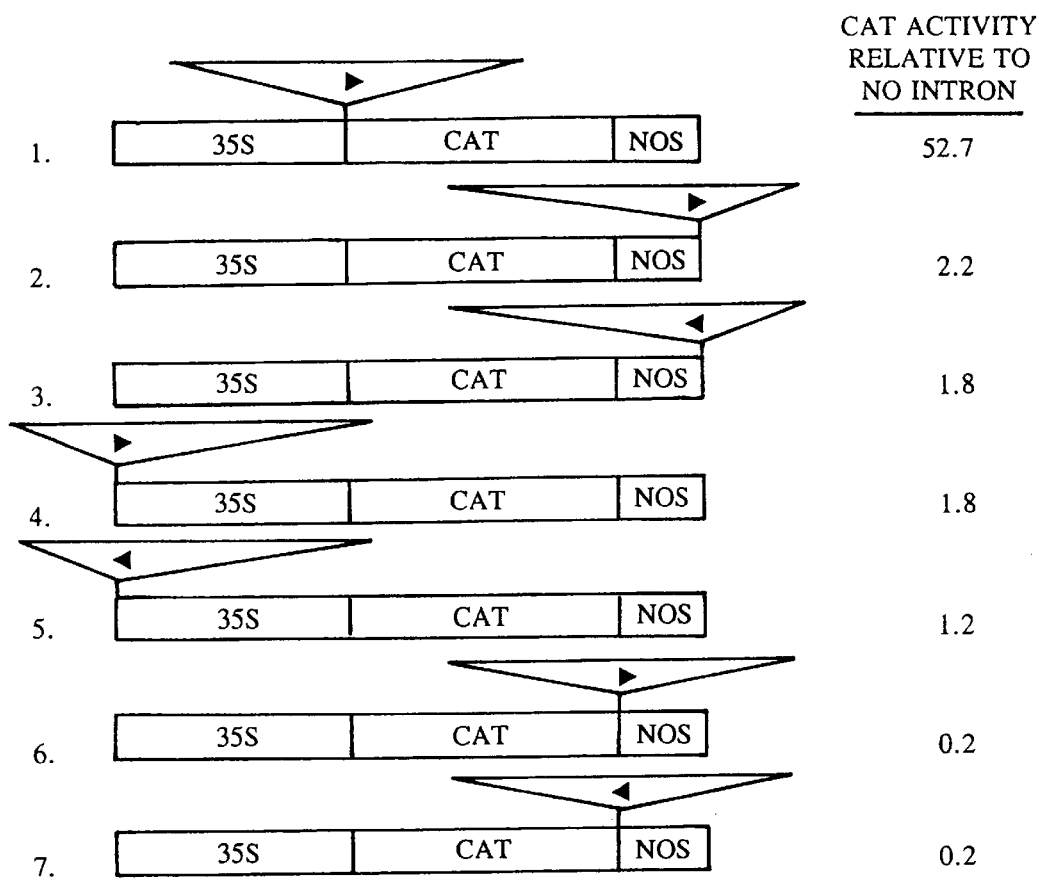
FIG. 4 shows placement of the Sh1 intron 1 cassette in chimeric gene constructions and relative CAT activities in transient expression assays. The Sh1 intron 1 cassette is denoted by the triangle and orientation is indicated by the arrow head. CAT activities are shown relative to the intronless construction p35SCN. Each value is the average of two separate electroporation experiments with duplicate electroporations and CAT enzyme assays within each experiment. The following values reflect the relative CAT activities in the two experiments: Construct 1, p35SIfSCN (29.6, 75.8); Construct 2 (3.3, 1.1); Construct 3 (2.7, 0.9); Construct 4 (2.2, 1.3); Construct 5 (1.6, 0.9); Construct 6 (0.4–0.1); and Construct 7 (0.3, 0.1).

The basic gene construction p35SCN shown in FIG. 3A contains the CAT reporter gene coupled to the NOS polyadenylation region, with transcription driven by the CaMV 35S promoter. The Sh1 intron 1 cassette consists of 10 bp exon 1, the 1028 bp intron and 17 bp exon 2, flanked by a 5' CC dinucleotide and a 3' C nucleotide which were generated by subcloning the Sh1 sequences. Initially the Sh1 intron cassette was incorporated into p35SCN in the region corresponding to the 5' untranslated leader of the mRNA. The construction p35SIfSCN shown in FIG. 3B contains the cassette in the normal orientation with respect to the direction of transcription. To examine the effect of placement of the Sh1 sequences on CAT gene expression, the cassette was inserted at three other positions in p35SCN. These constructions are shown in FIG. 4. The Sh1 intron 1 cassette was placed in both the normal and inverted orientations at each cloning site.

The Sh1 intron 1 cassette is most effective in stimulating CAT expression when placed in the 5'→3' orientation between the promoter and the reporter gene. The cassette increased gene expression an average of 53-fold at this position (FIG. 4, line 1). In the inverted orientation (p35SIrSCN), the Sh1 cassette did not stimulate CAT expression (see Example 7, supra). This optimum placement within the transcription unit is consistent with results obtained for the maize Adh1 first intron (Callis et al., 1987), rice actin first intron (McElroy et al., 1990) and maize Adh1 introns 2 and 6 (Mascarenhas et al., 1990).

Placement of the Sh1 intron 1 cassette in each orientation either 3' to the NOS polyadenylation region (FIG. 4, lines 2 and 3) or 5' to the promoter (FIG. 4, lines 4 and 5) had only a slight effect on CAT activity levels. The small stimulations of activity (1.2- to 2.2-fold average increases) probably reflect the range of experimental variation and are unlikely to be significant.

These observations indicate that the Sh1 first intron cassette must be transcribed and processed to fully stimulate gene expression. Position within the transcription unit is important, since the Sh1 first intron cassette in the 5' untranslated region gives rise to a substantial increase in gene activity, but placement of the cassette in the 3' untranslated region of the transcript reduces gene activity to a level below the intronless p35SCN (FIG. 4, lines 6 and 7).

Example 9

Effect of Multiple Copies of Sh1 Sequences on Gene Expression

Figure 5:
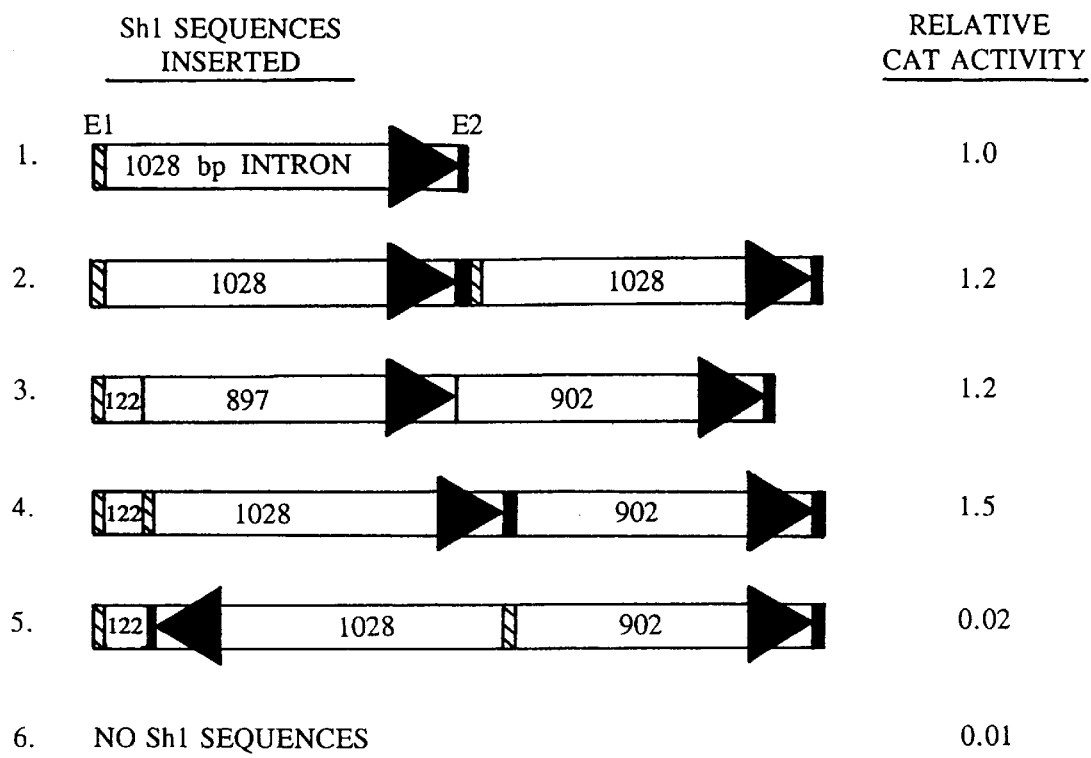
FIG. 5 shows relative CAT activities of gene constructions containing duplicated Sh1 sequences. CAT activities are averages of two separate electroporation experiments and are shown relative to p35SIfSCN, which contains a single copy of the Sh1 intron 1 cassette. Values given below are the relative CAT activities in the two experiments. Only the Sh1 sequences are diagrammed and all were placed in the 5' untranslated region of p35SCN as described hereinbelow. The Sh1 intron 1 cassette shown in line 1 (Construct 1) contains linker and Sh1 exon 1 sequences (E1, diagonally-lined box), the 1028 base pair (bp) intron, and exon 2 and linker sequences (E2, filled box). The large arrow head indicates the orientation of Sh1 sequences relative to the direction of transcription. Construct 2 comprises two copies of the cassette arrayed in tandem (1.1, 1.3). Construct 3 comprises an 897 bp internal fragment of the Sh1 intron 1 cloned at a blunt-ended SstI site within a complete Sh1 intron 1 cassette. The resultant augmented intron contains 1921 bp of Sh1 intron 1 sequences and one pair of splice junctions and exonic flanking sequences (1.2, 1.2). Construct 4 comprises two copies of the Sh1 intron 1 cassette, nested by inserting a complete cassette at a blunt-ended SstI site within the intron of another cassette. The nested arrangement contains two pairs of intron splice junctions and exonic flanking regions with all sequences in the 5'→3' orientation (1.3, 1.7). Construct 5 comprises nested arrangements of two Sh1 intron 1 cassette as in Construct 4, but with internal cassette in the inverted orientation (0.02, 0.02). Construct 6 is the intronless construct, p35SCN (0.01, 0.02).

Since one copy of the Sh1 first intron cassette greatly stimulates gene expression, we investigated whether the presence of multiple copies of the Sh1sequences would further increase CAT expression. Relative CAT activities of gene constructions were determined as described in Example 8. The relevant constructions and relative CAT activities are shown in FIG. 5. All inserted Sh1 sequences were placed in the 5' untranslated region between 35S promoter and the CAT gene. Two copies of the Sh1 intron 1 cassette arranged in tandem gave virtually the same stimulation of gene expression as a single copy (FIG. 5, lines 1 and 2). The magnitude of intron-mediated stimulation is not dependent on intron copy number, since the tandem arrangement of cassettes produced just 1.2 times the level of activity obtained with one cassette.

An 897 bp internal fragment of the Sh1 intron was placed within a complete copy of the cassette, with all Sh1 sequences in the normal 5'→3' orientation. This augmented arrangement of Sh1 sequences stimulated CAT activity to approximately the same level as the standard cassette (FIG. 5, line 3). A complete copy of the Sh1 intron 1 cassette was placed within another cassette, with the inserted cassette in either the normal or inverted orientation (FIG. 5, lines 4 and 5). When the nested Sh1 cassette was placed in the 5'→3' orientation, CAT activity levels were on average 1.5 times those observed for the single copy construction p35SCIfSCN. However, placement of the nested cassette in the inverted orientation reduced CAT activity to the level obtained with the intronless construction p35SCN (FIG. 5, lines 5 and 6).

The data presented in FIG. 5 shows that substantial alterations can be made within the sh1 first intron cassette without significantly affecting the enhancement of gene activity. The data further show that while some alterations within the intron are tolerated, the orientation of sequences is important since placement of an inverted Sh1 intron cassette within another cassette completely abolishes the stimulatory effect.

Example 10

Effect of Deletions Within the Sh1 Intron on Gene Expression

Since the stimulatory effect is not substantially altered when Sh1 intron and exon sequences are added in the normal orientation to a Sh1 intron 1 cassette, we investigated whether deletions within the intron would affect gene expression. As diagrammed in FIG. 6, eight overlapping deletions ranging from 226 bp to 649 bp were tested. CAT activity levels measured for the gene constructions containing these intron deletions varied only slightly from those of p35SIfSCN which contains the complete Sh1 intron 1 cassette. The smallest deletion, 226 bp, yielded 80% relative CAT activity. Five of the intron deletion constructions increased CAT activity relative to p35SIfSCN, but only 1.2 to 1.9 fold, levels considered to be within the range of experimental variation. The largest deletion, spanning 649 bp of the intron, gave CAT gene activity at the same level as p35SIfSCN. It is apparent from these results that the internal two-thirds of the Sh1 intron 1 is not required for stimulation of gene expression.

Example 11

Effect of Individual Sh1 Exon and Intron Regions on Gene Expression

The large Sh1 first intron cassette contains the 1028 bp intron, 27 bp of exon sequences and three additional cloning-derived nucleotide sequences. Ten AUG triplets reside within the intron and translation of an unspliced transcript would not give rise to wild-type CAT protein. Thus, it is highly probable that formation of an active CAT enzyme requires intron splicing. Splicing of the intron using Sh1 splice signals would leave 30 nucleotide inserted sequences. Accordingly, we synthesized constructions that contained only the Sh1 exon sequences to determine whether the increase in gene expression is due to these sequences. FIG. 7 presents the structure of the 5' leader region of p35SCN and shows the sequences of the polylinker cloning region and the Sh1 and Adh1 exon fragments. The influence of the Sh1 exon sequences on CAT activity was examined in three slightly different constructions, described in Table 5. In Table 5, the composition and size in bp of the maize sequences are described in the first and second columns. All exon sequences and exon/intron/exon combinations were placed in the 5' untranslated region of p35SCN as indicated in the Insertion Site column. CAT activities were determined for duplicate electroporations of each construct on each batch of protoplasts. All constructs were tested together in each of three protoplast preparations. Mean relative CAT activities are in boldface type and the values from the three experiments are shown in parentheses. Sequences were placed at two positions in the 5' untranslated region between the promoter and the CAT coding region. In the absence of an intron, Sh1 exon sequences stimulated CAT activity averages 4 to 7 fold (Table 5, line 1–3). The three constructions contained minor modifications of the Sh1 exon sequences. These alterations are significant because the differences in activity presented in Table 5 were seen in three separate experiments and in experiments not shown. The most effective exon sequence construction exactly reproduced the 27 bp in p35SCN at the same HincII site used for cloning of the complete Sh1 intron 1 cassette (Table 5, line 2).

The results demonstrate that these Sh1 exon sequences by themselves stimulate reporter gene expression. The degree of stimulation is affected by placement of the sequences in the polylinker and by removal of short regions at each end of the Sh1 exon fragment (2 nucleotides at the 5' end and 1 or 3 nucleotides at the 3' end). Since these Sh exon sequences increase CAT gene expression in constructions lacking the Sh1 first intron, it is likely that there are at least two mechanisms involved in the increased gene expression conditioned by the Sh1 intron 1 cassette. The mRNA produced from the most active Sh1 exon insertion (Table 5, line 1) would be identical to the processed message from p35SIfSCN (Table 5, line 4). This suggests that these Sh1 exon sequences in the 5' untranslated region increase translation efficiency or stability of the mRNA.

The ability of these Sh1 exon sequences to increase CAT activity contrasts with results for exon sequences flanking the Adh1 first intron. We tested these Adh1 exon and linker sequences and found a deleterious effect on gene expression when they were placed at either of two cloning sites in our reporter gene construction (Table 5, lines 6 and 7). In each case, CAT activity was reduced on average to about 40% of the level seen for the reference construction p35SCN. In the

TABLE 5

Relative CAT Activities: Adh1 and Sh1 exon sequences, cognate intron cassettes, and hybrid cassettes.

| | | | CAT Activity | |
|---|---|---|---|---|
| Exon Sequence | Intron | Insertion Site | Relative to p35SCN | Relative to p35SIfSCN |
| Sh1 | | | | |
| 1. CC/10 bp exon 1/ 17 bp exon 2/C | — | HincII (blunt) | 7.3 (14.3, 4.9, 2.7) | 0.22 (0.40, 0.09, 0.18) |
| 2. 10 bp exon 1/15 bp exon 2 | — | HincII (blunt) | 5.8 (12.4, 3.7, 1.3) | 0.17 (0.35, 0.07, 0.09) |
| 3. 10 bp exon 1/17 bp exon 2 | — | 5':BamHI(blunt 3':AccI(cohesive) | 3.9 (6.1, 4.5, 1.1) | 0.11 (0.17, 0.08, 0.08) |
| 4. 5':CC/10 bp exon 1 3':17 bp exon 2/C | 1028 bp Sh1 intron 1 | HincII(blunt) | 35.8 (35.6, 56.5, 15.2) | 1.00 |
| 5. 5':CC/10 bp exon 1 3':17 bp exon 2/C | 534 bp Adh1 intron 1 | HincII(blunt) | 0.6 (0.4, 1.0, 0.4) | 0.02 (0.01, 0.02, 0.03) |
| Adh1 | | | | |
| 6. 14 bp exon 1/ 6 bp exon 2/7 bp linker | — | BamHI(cohesive) | 0.4 (0.7, 0.1, 0.2) | 0.01 (0.02, 0.002, 0.01) |
| 7. 14 bp exon 1/ 6 bp exon 2/7 bp linker | — | HincII(blunt) | 0.4 (0.7, 0.1, 0.3) | 0.01 (0.02, 0.002, 0.02) |
| 8. 5':14 bp exon 1 3':6 bp exon 2/7 bp linker | 534 bp Adh1 intron 1 | BamHI(cohesive) | 2.4 (4.3, 1.3, 1.6) | 0.08 (0.12, 0.02, 0.10) |
| 9. 5':14 bp exon 1 3':6 bp exon 2/7 bp linker | 1028 bp Sh1 intron 1 | HincII(blunt) | 43.3 (19.5, 88.7, 21.6) | 1.18 (0.55, 1.57, 1.42) | exon sequences, 3 bp linker sequences and the cloning site used in generating p35SIfSCN, lacking only the 1028 bp Sh1 intron. This construction increased CAT activity in three experiments an average 7.3-fold relative to p35SCN (Table 5, line 1). This is 22% of the average stimulation caused by the complete Sh1 intron 1 cassette. Constructions containing Sh1 exon sequences shortened by 3 or 5 bp and placed at a different polylinker also stimulated CAT expression, but to a lesser extent. A construction containing the 27 bp of Sh1 exon sequences but lacking the cloning-derived 5' CC dinucleotide and 3' C nucleotide stimulated CAT levels an average 3.9 fold when placed between BamHI and AccI sites (Table 5, line 3). An average 5.8-fold stimulation was observed when 10 bp exon 1 plus 15 bp exon 2 was placed same set of experiments, the Adh1 intron 1 complete with flanking sequences stimulated gene expression an average of 2.4 fold (Table 5, line 8).

While the Sh1 exon sequences increase gene expression, the Adh1 exon sequences do not. This difference was utilized to further evaluate the individual contributions of the intron and the flanking exon sequences to the stimulation of CAT expression. Combining the Adh1 and Sh1 flanking sequences with their respective non-cognate introns could indicate whether the intron and exon regions have separable additive or multiplicative effects or point to more complex interactions. We synthesized hybrid cassettes containing the Sh1 exon and linker sequences flanking the Adh1 first intron, and conversely, the Adh1 exon and linker regions flanking the Sh1 first intron. The construction containing the Adh1 exon/Sh1 intron/Adh1 exon cassette increased CAT expression an average of 43 fold relative to p35SCN in three experiments (Table 5, line 9). Unexpectedly, this level of stimulation was approximately 1.2 times that observed for the standard Sh1 intron 1 cassette in the same set of three experiments. Even more surprisingly, the hybrid Sh1 exon/Adh1 intron/Sh1 exon cassette decreased CAT expression to 60% of the level seen for the intronless construct p35SCN (Table 5, line 5). This hybrid cassette might be expected to show a level of gene expression reflecting both the influence of the Adh1 intron 1 and the increased expression conditioned by Sh1 exon sequences. Sequencing of the exon/intron hybrid junctions and most of the intron revealed no PCR-generated errors or other sequence deviations.

Compared to the Sh1 exon sequences, the Adh1 sequences were ineffective in increasing gene expression in the absence of an intron. However, the combination of the Adh1 flanking sequences with the Sh1 intron gave greater stimulation even though the enhancing effect of the Sh1 exon sequences had been removed. Conversely, a cassette containing Sh1 sequences flanking the Adh1 intron 1 decreased the level of CAT expression. It is possible that the novel exon/intron junctions in each hybrid cassette result in altered splicing efficiencies. The hybrid Adh1/Sh1 splice junctions are compared with the cognate junctions and the monocot/dicot plant consensus (Goodall, G. J., and W. Filipowicz (1991) *EMBO J.* 10:2635–2644 and Goodall, G. J., et al. (1991) *Oxford Surveys of Plant Molecular and Cellular Biology* (Oxford University Press) 7:256–296) in Table 6. The strengths of the 3' splice junctions are equivalent, as judged by conformity to the consensus sequence. Each exon/intron/exon combination shows just one deviation from the 3' consensus sequence, in all cases at the +1 position. However, the expected splicing efficiencies for the hybrid 5' splice junctions correlate well with the observed reporter gene expression patterns. The hybrid Adh1/Sh1/Adh1 cassette has just one mismatch in the 5' splice sequence (Table 6, line 3) and this cassette increased gene expression 1.2 fold above that of the Sh1/Sh1/Sh1 cassette. The latter cassette has two deviations from the consensus signal (Table 6, line 2). The Sh1/Adh1/Sh1 combination has three mismatches in the 5' splice junction (Table 6, line 4) and this cassette failed to increase gene expression.

It should be understood that the examples and embodiments described herein are for illustrative purposes only and that various modifications or changes in light thereof will be suggested to persons skilled in the art and are to be included within the spirit and purview of this application and the scope of the appended claims.

TABLE 6

Comparison of Splice Sites in Adh1 and Sh1 intron 1 cassettes and hybrid cassettes

| Exon/Intron/Exon Combination | 5' Junction | | | | | | | 3' Junction | | | | | |
|---|---|---|---|---|---|---|---|---|---|---|---|---|---|
| | -2 | -1/ | +1 | +2 | +3 | +4 | +5 | -5 | -4 | -3 | -2 | -1/ | +1 |
| 1. Consensus[a] | A | G/ | G | T | A | A | G | T | G | C | A | G/ | G |
| 2. Sh1/Sh1/Sh1 | G | G/ | G | T | A | T | G | T | G | C | A | G/ | T |
| 3. Adh1/Sh1/Adh1 | A | G/ | G | T | A | T | G | T | G | C | A | G/ | C |
| 4. Sh1/Adh1/Sh1 | G | G/ | G | T | C | C | G | T | G | C | A | G/ | T |
| 5. Adh1/Adh1/Adh1 | A | G/ | G | T | C | C | G | T | G | C | A | G/ | C |

[a]Monocot and dicot plant splice site consensus signals (Goodall and Filipowicz, 1991; Goodall et al., 1991)
Underlined bases are deviations from the consensus sequence.

We claim:

1. A method for increasing the expression rate of a gene in a plant cell, said method comprising the steps of:
   (a) inserting an intron into said gene, the intron comprising a 5' splice site of the Sh1 first intron and a 3' splice site of the Sh1 first intron, the 5' splice site being situated closer to the 5' end of said gene than the 3' splice site, said intron being inserted between a transcription start site and a translation start site of said gene, and said intron increasing the expression of a downstream coding sequence thereby forming an intron-modified gene; and
   (b) introducing said intron-modified gene into a plant cell such that said gene is expressed under the control of said intron in said plant cell, whereby the expression rate of said gene is increased as compared to an unmodified gene.

2. The method of claim 1 wherein said intron has a nucleotide sequence as set forth in from about nucleotide 53 through about nucleotide 1080 or functionally equivalent duplications or modifications in length or minor sequence variations that do not significantly effect function.

3. The method of claim 2 wherein said intron further comprises from about 1 to about 50 additional nucleotides on either end of said intron, wherein said additional nucleotides comprise sequences of exon 1 and exon 2 or functionally equivalent duplications or modifications in length or minor sequence variations that do not significantly effect function, and wherein said exon 1 and exon 2 are flanking sequences adjacent to intron 1 of the Sh1 locus of maize.

4. The method of claim 2 wherein said intron further comprises from about 1 to about 50 additional nucleotides on either end of said intron, wherein said additional nucleotides comprise sequences of exon 1 and exon 2 or functionally equivalent duplications or modifications in length or minor sequence variations that do not significantly effect function, and wherein said exon 1 and exon 2 are exon sequences adjacent to intron 1 of the Adh locus of maize.

5. The method of claim 2 wherein said intron further comprises a nucleotide insert having from about 1 to about 1080 nucleotides, said nucleotide insert being inserted between the 5' splice site of the Sh1 first intron and the 3' splice site of the Sh1 first intron, and wherein said nucleotide insert lacks an intron splice site in an opposite orientation to said 5' splice site and said 3'splice site of the Sh1 first intron.

6. The method of claim 1 wherein said 5' splice site has a nucleotide sequence as set forth in SEQ ID NO:1 from about nucleotide 53 to about nucleotide 452 and said 3' splice site comprises a nucleotide sequence as set forth in SEQ ID NO:1 from about nucleotide 736 to about nucleotide 1080 or functionally equivalent duplications or modifications in length or minor sequence variations that do not significantly effect function of the 5' or 3' splice sites.

7. The method of claim 1 wherein said 5' splice site has a nucleotide sequence as set forth in SEQ ID NO:1 from about nucleotide 53 to about nucleotide 400 and said 3' splice site comprises a nucleotide sequence as set forth in SEQ ID NO:1 from about nucleotide 823 to about nucleotide 1080 or functionally equivalent duplications or modifications in length or minor sequence variations that do not significantly effect function of the 5' or 3' splice sites.

8. The method of claim 1 wherein said 5' splice site has a nucleotide sequence as set forth in FIG. 1A from about nucleotide 53 to about nucleotide 178 and said 3' splice site comprises a nucleotide sequence as set forth in FIG. 1A from about nucleotide 736 to about nucleotide 1080 or functionally equivalent duplications or modifications in length or minor sequence variations that do not significantly effect function of the 5' or 3' splice sites.

9. The method of claim 1 wherein said 5' splice site has a nucleotide sequence as set forth in FIG. 1A from about nucleotide 53 to about nucleotide 178 and said 3' splice site comprises a nucleotide sequence as set forth in FIG. 1A from about nucleotide 452 to about nucleotide 1080 or functionally equivalent duplications or modifications in length or minor sequence variations that do not significantly effect function of the 5' or 3' splice sites.

10. The method of claim 1 wherein said 5' splice site has a nucleotide sequence as set forth in SEQ ID NO:1 from about nucleotide 53 to about nucleotide 452 and said 3' splice site comprises a nucleotide sequence as set forth in FIG. 1A from about nucleotide 823 to about nucleotide 1080 or functionally equivalent duplications or modifications in length or minor sequence variations that do not significantly effect function of the 5' or 3' splice sites.

11. The method of claim 1 wherein said 5' splice site has a nucleotide sequence as set forth in FIG. 1A from about nucleotide 53 to about nucleotide 178 and said 3' splice site comprises a nucleotide sequence as set forth in FIG. 1A from about nucleotide 823 to about nucleotide 1080 or functionally equivalent duplications or modifications in length or minor sequence variations that do not significantly effect function of the 5' or 3' splice sites.

12. The method of claim 1 wherein said 5' splice site has a nucleotide sequence as set forth in FIG. 1A from about nucleotide 53 to about nucleotide 400 and said 3' splice site comprises a nucleotide sequence as set forth in FIG. 1A from about nucleotide 736 to about nucleotide 1080 or functionally equivalent duplications or modifications in length or minor sequence variations that do not significantly effect function of the 5' or 3' splice sites.

13. The method of claim 1 wherein said 5' splice site has a nucleotide sequence as set forth in FIG. 1A from about nucleotide 53 to about nucleotide 178 and said 3' splice site comprises a nucleotide sequence as set forth in FIG. 1A from about nucleotide 400 to about nucleotide 1080 or functionally equivalent duplications or modifications in length or minor sequence variations that do not significantly effect function of the 5' or 3' splice sites.

14. The method of claim 11 wherein said intron further comprises from about 1 to about 50 additional nucleotides on either end of said intron, wherein said additional nucleotides comprise sequences of exon 1 and exon 2 functionally equivalent duplications or modifications in length or minor sequence variations that do not significantly effect function and wherein said exon 1 and exon 2 are exon sequences adjacent to intron 1 of the Sh1 locus of maize.

15. The method of claim 11 wherein said intron further comprises from about 1 to about 50 additional nucleotides on either end of said intron, wherein said additional nucleotides comprise sequences of exon 1 and exon 2 or functionally equivalent duplications or modifications in length or minor sequence variations that do not significantly effect function and wherein said exon 1 and exon 2 are exon sequences adjacent to intron 1 of the Adh locus of maize.

16. The method of claim 1 wherein said host system is selected from the group consisting of plant tissue, a plant cell, a yeast, a bacterium, an insect cell and a mammalian cell.

17. The method of claim 16 wherein said plant tissue or plant cell is from a monocotyledonous plant.

18. The method of claim 1 wherein said gene is a plant-expressible gene and wherein said plant-expressible gene is expressed in plant tissue.

19. The method of claim 18 wherein said plant tissue is from a monocotyledonous plant.

20. The method of claim 19 wherein said monocotyledonous plant is selected from the group consisting of *Panicum maximum, Pennisetum purpureum*, and *Zea mays*.

21. The method of claim 1 wherein said intron-modified gene further comprises a promoter and wherein said intron is inserted into said intron-modified gene 3' to said promoter and 5' to a translation start site.

22. The method of claim 21 wherein said promoter is a CaMV 35S promoter or an Sh1 promoter.

23. The method of claim 1 wherein said intron-modified gene is introduced into said plant cell by a technique for introducing foreign DNA sequences into plant tissue wherein said technique is electroporation, ballistic transformation, T-DNA mediated transformation or microinjection.

24. The method of claim 1 wherein said intron-modified gene is introduced into said plant cell by electroporation.

25. A method for increasing the expression rate of a gene in a plant cell, said method comprising the steps of:

(a) inserting exon DNA sequences into said gene, the exon DNA sequences corresponding to FIG. 1A from position 43 to 52 and from position 1081 to 1097, said exon DNA sequences being inserted between a transcription start site and a translation start site of said gene, said exon DNA sequences increasing the expression of an associated coding sequence, thereby forming an exon-modified gene; and (b) introducing said exon-modified gene into a host plant cell such that said gene is expressed under the control of said exon DNA sequences in said host system, whereby the expression rate of said gene is increased as compared to an unmodified gene.

26. The method of claim 25 wherein said exon DNA sequences further comprise a 5' CC dinucleotide and 3' C nucleotide.

27. An intron-modified gene comprising a 5' splice site of the Sh1 first intron and a 3' splice site of the Sh1 first intron, the splice sites being inserted in normal 5' to 3' orientation into a 5'-untranslated region of the gene between a start site of transcription and a start site of translation.

28. The intron-modified gene of claim 27 comprising a nucleotide sequence as a set forth in FIG. 1A from about nucleotide 53 through about nucleotide 1080 or functionally equivalent duplications or modifications in length or minor sequence variations that do not significantly effect function of the 5' or 3' splice sites.

29. The intron-modified gene of claim 28 further comprising from 1 to about 50 additional nucleotides on either end of said nucleotide sequence, wherein said additional nucleotides comprise sequences of exon 1 and exon 2 or functionally equivalent duplications or modifications in length or minor sequence variations that do not significantly effect function and wherein said exon 1 and exon 2 are flanking sequences adjacent to intron 1 of the Sh1 locus of maize.

30. The intron-modified gene of claim 28 further comprising from 1 to about 50 additional nucleotides on either end of said nucleotide sequence, wherein said additional nucleotides comprise sequences of exon 1 and exon 2 or functionally equivalent duplications or modifications in length or minor sequence variations that do not significantly effect function and wherein said exon 1 and exon 2 are flanking sequences adjacent to intron 1 of the Adh locus of maize.

31. The intron-modified gene of claim 28 further comprising a nucleotide insert having from 1 to about 1080 nucleotides, said nucleotide insert being inserted between the 5' splice site of the Sh1 first intron and the 3' splice site of the Sh1 first intron, and wherein said nucleotide insert lacks an intron splice site in an opposite orientation to said 5' splice site and said 3'splice site of the Sh1 first intron.

32. The intron-modified gene of claim 27 further wherein said 5' splice site has a nucleotide sequence as set forth in SEQ ID NO:1 from about nucleotide 53 to about nucleotide 452 and said 3' splice site comprises a nucleotide sequence as set forth in SEQ ID NO:1 from about nucleotide 736 to about nucleotide 1080 or functionally equivalent duplications or modifications in length or minor sequence variations that do not significantly effect function of the 5' or 3' splice sites.

33. The intron-modified gene of claim 27 wherein said 5' splice site has a nucleotide sequence as set forth in FIG. 1A from about nucleotide 53 to about nucleotide 400 and said 3' splice site comprises a nucleotide sequence as set forth in FIG. 1A from about nucleotide 823 to about nucleotide 1080 or functionally equivalent duplications or modifications in length or minor sequence variations that do not significantly effect function of the 5 or 3' splice sites.

34. The intron-modified gene of claim 27 wherein said 5' splice site has a nucleotide sequence as set forth in FIG. 1A from about nucleotide 53 to about nucleotide 178 and said 3' splice site comprises a nucleotide sequence as set forth in FIG. 1A from about nucleotide 736 to about nucleotide 1080 or functionally equivalent duplications or modifications in length or minor sequence variations that do not significantly effect function of the 5' or 3' splice sites.

35. The intron-modified gene of claim 27 wherein said 5' splice site has a nucleotide sequence as set forth in FIG. 1A from about nucleotide 53 to about nucleotide 178 and said 3' splice site comprises a nucleotide sequence as set forth in FIG. 1A from about nucleotide 452 to about nucleotide 1080 or functionally equivalent duplications or modifications in length or minor sequence variations that do not significantly effect function of the 5' or 3' splice sites.

36. The intron-modified gene of claim 27 wherein said 5' splice site has a nucleotide sequence as set forth in FIG. 1A from about nucleotide 53 to about nucleotide 452 and said 3' splice site comprises a nucleotide sequence as set forth in FIG. 1A from about nucleotide 823 to about nucleotide 1080 or functionally equivalent duplications or modifications in length or minor sequence variations that do not significantly effect function of the 5' or 3' splice sites.

37. The intron-modified gene of claim 27 wherein said 5' splice site has a nucleotide sequence as set forth in FIG. 1A from about nucleotide 53 to about nucleotide 178 and said 3' splice site comprises a nucleotide sequence as set forth in FIG. 1A from about nucleotide 823 to about nucleotide 1080 or functionally equivalent duplications or modifications in length or minor sequence variations that do not significantly effect function of the 5' or 3' splice sites.

38. The intron-modified gene of claim 27 wherein said 5' splice site has a nucleotide sequence as set forth in FIG. 1A from about nucleotide 53 to about nucleotide 400 and said 3' splice site comprises a nucleotide sequence as set forth in FIG. 1A from about nucleotide 736 to about nucleotide 1080 or functionally equivalent duplications or modifications in length or minor sequence variations that do not significantly effect function of the 5' or 3' splice sites.

39. The intron-modified gene of claim 27 wherein said 5' splice site has a nucleotide sequence as set forth in FIG. 1A from about nucleotide 53 to about nucleotide 178 and said 3' splice site comprises nucleotide sequence as set forth in FIG. 1A from about nucleotide 400 to about nucleotide 1080 or functionally equivalent duplications or modifications in length or minor sequence variations that do not signifecantly effect function of the 5' or 3' splice sites.

40. The intron-modified gene of claim 27 further comprising a promoter and wherein the intron is inserted into said intron-modified gene 3' to said promoter and 5' to a translation start site.

41. The intron-modified gene of claim 40 wherein said promoter is a CaMV 35S promoter or an Sh1 promoter.

42. An exon-modified gene comprising exon DNA sequences corresponding to FIG. 1A from position 43 to 52 and from position 1081 to 1097.

43. The exon-modified gene of claim 42 wherein said exon DNA sequences further comprise a 5' CC dinucleotide and 3' C nucleotide.

44. An exon-modified gene comprising exon DNA sequences corresponding to SEQ ID NO:2.

45. An exon-modified gene comprising exon DNA sequences corresponding to SEQ ID NO:3.

46. A gene construct selected from the group consisting of pShIfSCN, p35SIfSCN and 35SIfACN.

\* \* \* \* \*

UNITED STATES PATENT AND TRADEMARK OFFICE
CERTIFICATE OF CORRECTION

PATENT NO. : 5,955,330

DATED : September 21, 1999

Page 1 of 2

INVENTOR(S) : Vasil et al.

It is certified that error appears in the above-identified patent and that said Letters Patent is hereby corrected as shown below:

On the Title Page, under [63], line 2, please delete "continuation" and replace with --continuation-in-part--.
On the Title Page, under [56], in the last line of the "Sheldon" reference, please delete "Sh,"" and
    replace with --Sh1,"--.
On Sheet 13 of 13, in Fig. 7C, please delete the first "A" in the sequence, so that it reads --GATCAA ...--.
In Column 1, line 5, please delete "continuation" and replace with --continuation-in-part--.
In Column 1, line 30, please delete "stimulate" and replace with --stimulates--.
In Column 9, line 20, please delete "CDNA" and replace with --cDNA--.
In Column 13, line 30, please delete "sequences" and replace with --sequence--.
In Column 13, line 34, please delete "and".
In Column 13, line 40, please delete "bp" and replace with --10 bp--.
In Column 13, line 42, please delete "sequences" and replace with --sequence--.
In Column 13, line 64, please delete "sequences" and replace with --sequence--.
In Column 18, line 21, please delete "sh1" and replace with --Sh1--.
In Column 31, line 17, after "in", please insert --plant tissue or--.
In Column 31, line 36, please delete "effect" and replace with --affect--.
In Column 31, line 42, please delete "effect" and replace with --affect--.
In Column 31, line 50, please delete "effect" and replace with --affect--.
In Column 31, line 67, please delete "effect" and replace with --affect--.
In Column 32, line 21, please delete "effect" and replace with --affect--.
In Column 32, line 28, please delete "effect" and replace with --affect--.
In Column 32, line 36, please delete "effect" and replace with --affect--.
In Column 32, line 45, please delete "effect" and replace with --affect--.
In Column 32, line 52, please delete "effect" and replace with --affect--.
In Column 32, line 60, please delete "effect" and replace with --affect--.
In Column 33, line 1, please delete "effect" and replace with --affect--.
In Column 33, line 8, please delete "effect" and replace with --affect--.
In Column 33, line 16, please delete "effect" and replace with --affect--.

UNITED STATES PATENT AND TRADEMARK OFFICE
CERTIFICATE OF CORRECTION

PATENT NO. : 5,955,330

DATED : September 21, 1999

INVENTOR(S) : Vasil et al.

Page 2 of 2

It is certified that error appears in the above-identified patent and that said Letters Patent is hereby corrected as shown below:

In Column 33, line 59, please delete "system," and replace with --plant cell,--.
In Column 34, line 7, please delete "effect" and replace with --affect--.
In Column 34, line 14, please delete "effect" and replace with --affect--.
In Column 34, line 23, please delete "effect" and replace with --affect--.
In Column 34, line 33, please delete "further".
In Column 34, line 40, please delete "effect" and replace with --affect--.
In Column 34, line 49, please delete "effect" and replace with --affect--.
In Column 34, line 57, please delete "effect" and replace with --affect--.
In Column 34, line 65, please delete "effect" and replace with --affect--.
In Column 35, line 6, please delete "effect" and replace with --affect--.
In Column 35, line 14, please delete "effect" and replace with --affect--.
In Column 35, line 22, please delete "effect" and replace with --affect--.
In Column 36, lines 4-5, please delete "signifecantly effect" and replace with --significantly affect--.
In Column 36, line 23, please delete "35SIfACN." and replace with --p35SIfACN--.

Signed and Sealed this

First Day of August, 2000

Attest:

Attesting Officer

Q. TODD DICKINSON

Director of Patents and Trademarks